(12) United States Patent
Nourian et al.

(10) Patent No.: US 9,463,078 B2
(45) Date of Patent: Oct. 11, 2016

(54) DEVICE AND PROCEDURE FOR IMPLANTING A DENTAL IMPLANT

(71) Applicant: Nobel Biocare Services AG, Kloten (CH)

(72) Inventors: Pedram Nourian, Tustin, CA (US); Steven M. Hurson, Yorba Linda, CA (US)

(73) Assignee: NOBEL BIOCARE SERVICES AG, Kloten (CH)

( * ) Notice: Subject to any disclaimer, the term of this patent is extended or adjusted under 35 U.S.C. 154(b) by 0 days.

(21) Appl. No.: 14/495,681

(22) Filed: Sep. 24, 2014

(65) Prior Publication Data
US 2015/0132710 A1 May 14, 2015

Related U.S. Application Data

(63) Continuation of application No. 13/260,252, filed as application No. PCT/EP2009/006535 on Sep. 9, 2009, now Pat. No. 8,876,530.

(60) Provisional application No. 61/095,923, filed on Sep. 10, 2008.

(51) Int. Cl.
*A61C 5/00* (2006.01)
*A61C 1/08* (2006.01)
*A61C 8/00* (2006.01)

(52) U.S. Cl.
CPC .............. *A61C 1/084* (2013.01); *A61C 8/0089* (2013.01)

(58) Field of Classification Search
CPC .... A61C 8/0089; A61C 1/084; A61C 1/082; A61B 17/1637; A61B 17/176
See application file for complete search history.

(56) References Cited

U.S. PATENT DOCUMENTS

| | | |
|---|---|---|
| 3,499,222 A | 3/1970 | Edelman et al. |
| 3,732,621 A | 5/1973 | Bostrom |
| 3,866,510 A | 2/1975 | Eibes et al. |
| 4,359,318 A | 11/1982 | Gittleman |
| 4,431,416 A | 2/1984 | Niznick |
| 4,531,916 A | 7/1985 | Scantlebury et al. |

(Continued)

FOREIGN PATENT DOCUMENTS

| | | |
|---|---|---|
| DE | 195 10 372 | 7/1996 |
| EP | 1 145 691 | 10/2001 |

(Continued)

OTHER PUBLICATIONS

International Search Report for International Application No. PCT/EP2009/006535 filed Sep. 9, 2009, mailed Feb. 26, 2010.

(Continued)

*Primary Examiner* — Heidi M Eide
(74) *Attorney, Agent, or Firm* — Knobbe, Martens, Olson & Bear LLP

(57) ABSTRACT

Various tools and procedures are provided for implantation of an implant at a target site. The procedure can include performing an osteotomy at the target site; placing a guide sleeve into the osteotomy; inserting a coring tool into the guide sleeve; coring the target site up to a depth less than the depth of the osteotomy, the coring tool being configured to collect autogenous bone material from the target site during the coring of the target site; placing the implant at the implant site; and grafting the autogenous bone material into selected portions of the target site.

2 Claims, 24 Drawing Sheets

(56) References Cited

U.S. PATENT DOCUMENTS

| | | | |
|---|---|---|---|
| 4,738,623 A | | 4/1988 | Driskell |
| 4,787,848 A | | 11/1988 | Ross |
| 4,790,753 A | | 12/1988 | Fradera |
| 4,998,881 A | * | 3/1991 | Lauks .................. 433/173 |
| 5,118,294 A | * | 6/1992 | Kurer .................. 433/220 |
| 5,120,223 A | | 6/1992 | Weissman |
| 5,254,005 A | | 10/1993 | Zuest |
| 5,259,398 A | | 11/1993 | Vrespa |
| 5,366,374 A | | 11/1994 | Vlassis |
| 5,433,607 A | | 7/1995 | Schmid et al. |
| 5,470,230 A | | 11/1995 | Daftary et al. |
| 5,591,029 A | | 1/1997 | Zuest |
| 5,622,500 A | | 4/1997 | Niznick |
| 5,702,346 A | | 12/1997 | Lazzara et al. |
| 5,817,098 A | * | 10/1998 | Albrektsson et al. ......... 606/96 |
| 5,871,356 A | | 2/1999 | Guedj |
| 5,888,034 A | | 3/1999 | Greenberg |
| 5,989,028 A | | 11/1999 | Niznick |
| 6,287,117 B1 | | 9/2001 | Niznick |
| 6,394,809 B2 | | 5/2002 | Rogers et al. |
| 6,953,426 B2 | | 10/2005 | Barber et al. |
| 8,128,402 B2 | | 3/2012 | Lundgren |
| 2001/0004711 A1 | | 6/2001 | Lazzara et al. |
| 2002/0160335 A1 | | 10/2002 | Ashman et al. |
| 2005/0042574 A1 | | 2/2005 | Lazarof |
| 2005/0164146 A1 | | 7/2005 | Cantor |
| 2006/0194171 A1 | | 8/2006 | Lazarof |
| 2008/0003539 A1 | | 1/2008 | Lundgren |
| 2008/0280254 A1 | | 11/2008 | Ackermann |
| 2010/0062389 A1 | | 3/2010 | Drews et al. |

FOREIGN PATENT DOCUMENTS

| | | |
|---|---|---|
| EP | 1 430 843 | 6/2004 |
| GB | 1 203 093 | 8/1970 |
| JP | 62-039711 | 2/1987 |
| JP | 63-207541 | 8/1988 |
| JP | 09 187467 | 7/1997 |
| JP | 2008-508931 | 3/2008 |
| WO | WO 91/14404 | 10/1991 |
| WO | WO 02/09598 | 2/2002 |
| WO | WO 2006/014130 | 2/2006 |
| WO | WO 2008/089885 | 7/2008 |
| WO | WO 2008/149822 | 12/2008 |

OTHER PUBLICATIONS

Park et al. "Survival Analysis of Wide-Diameter Implants in Maxillary & Mandibular Molar Regions; A Retrospective Study". The Journal of Korean Academy of Periodontology. vol. 37, No. 4 pp. 825-838, 2007.

Sartori et al., "Short Implants: an alternative treatment option". Quintessenza Internazionale, Implantology Special 2008. Sep.-Oct. 2008, Issue No. 5 pp. 111-116.

* cited by examiner

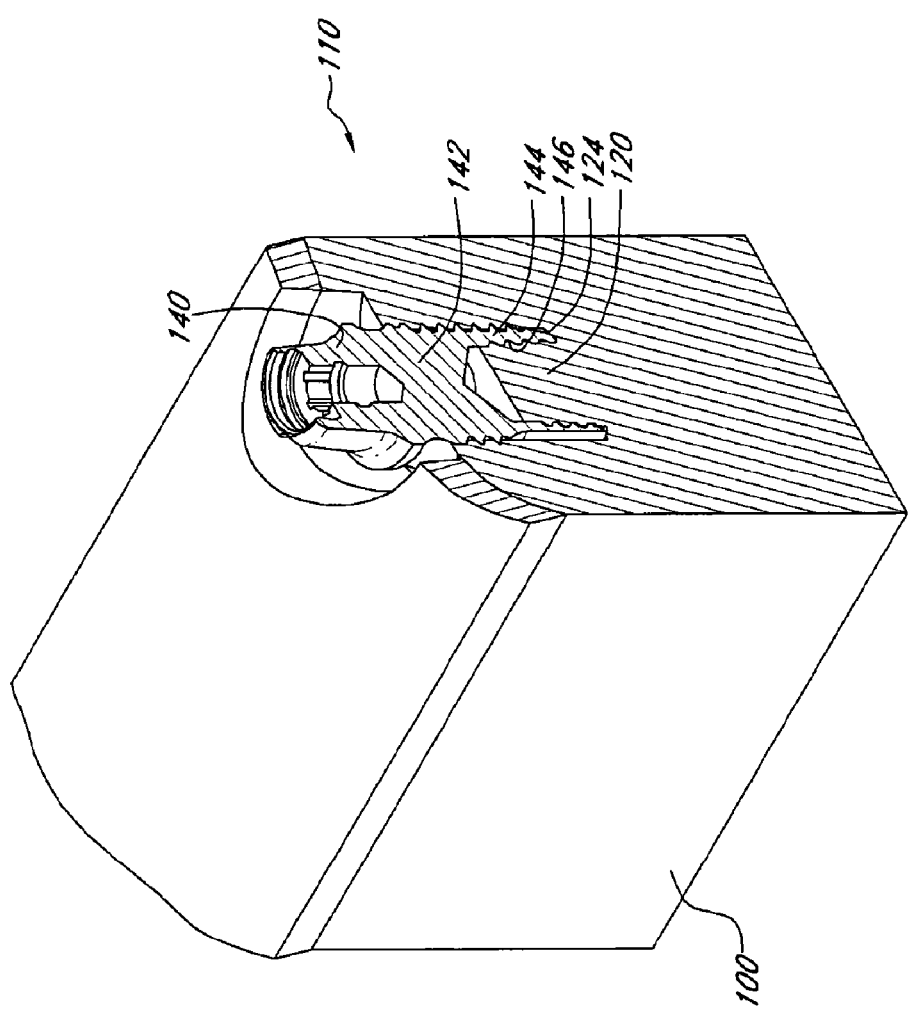

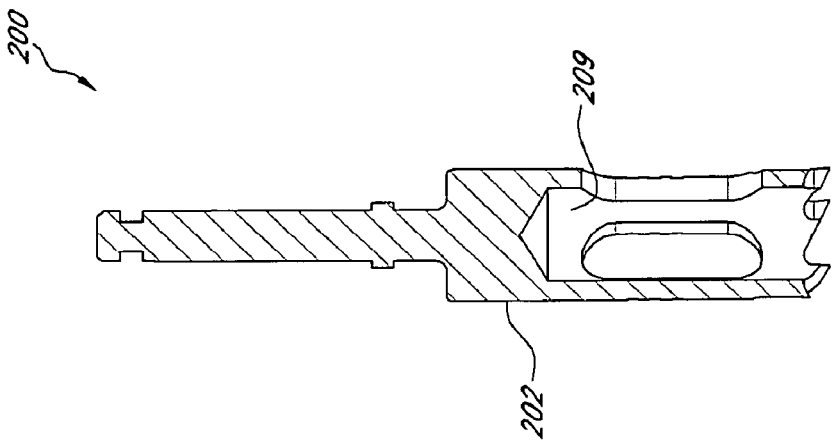
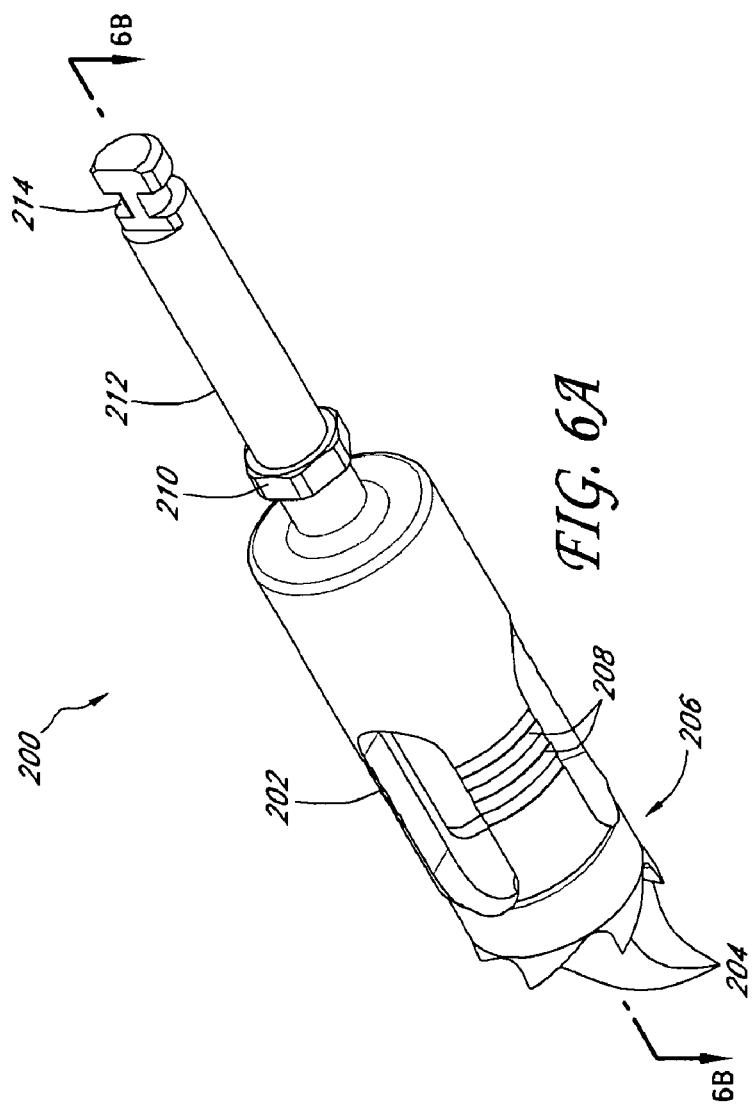

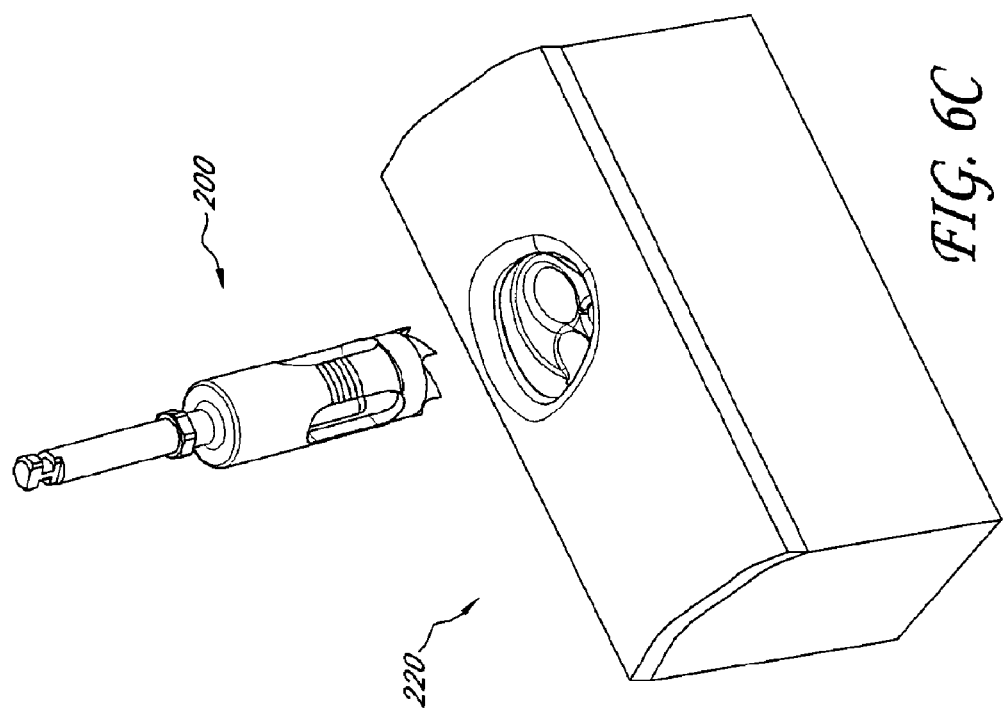

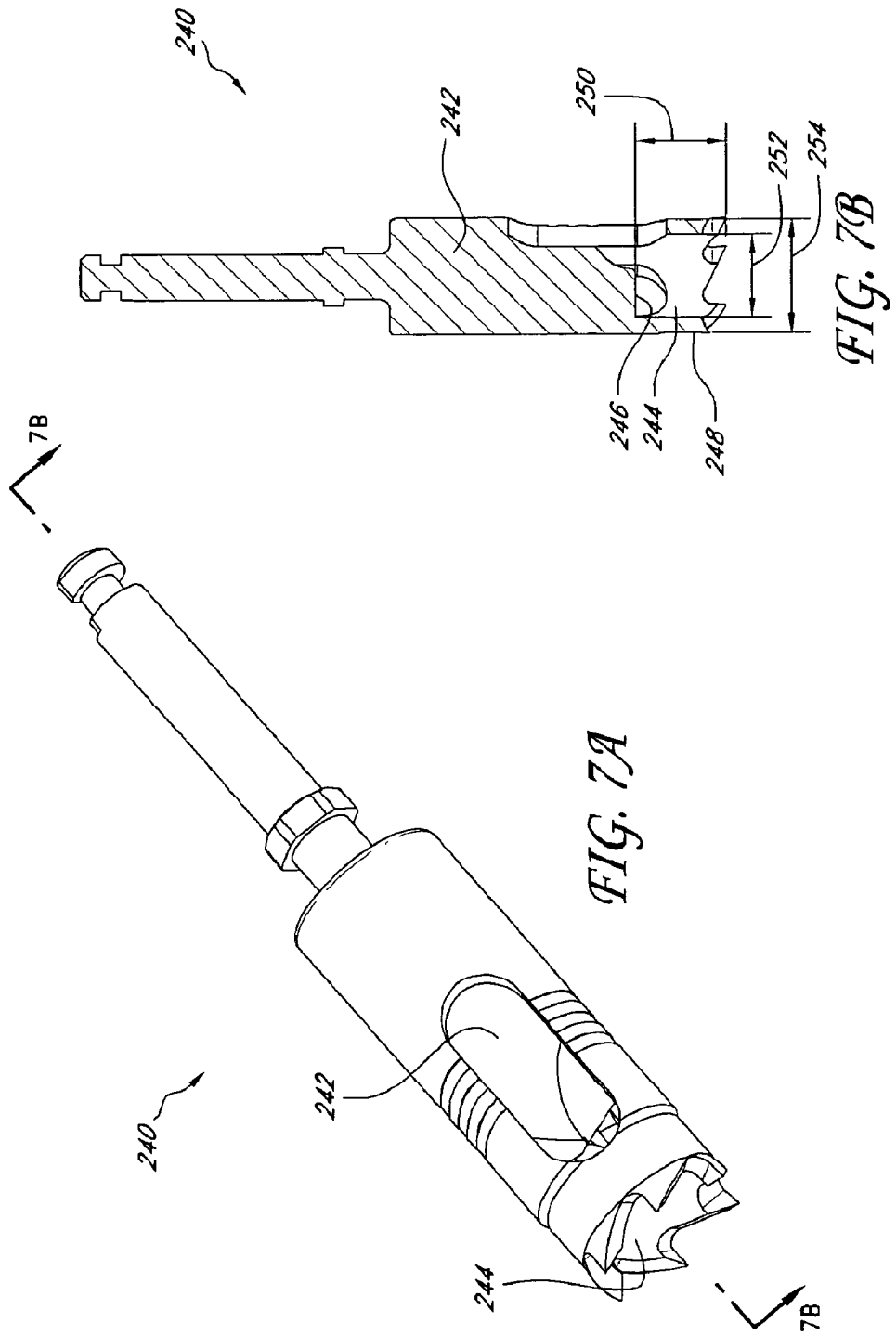

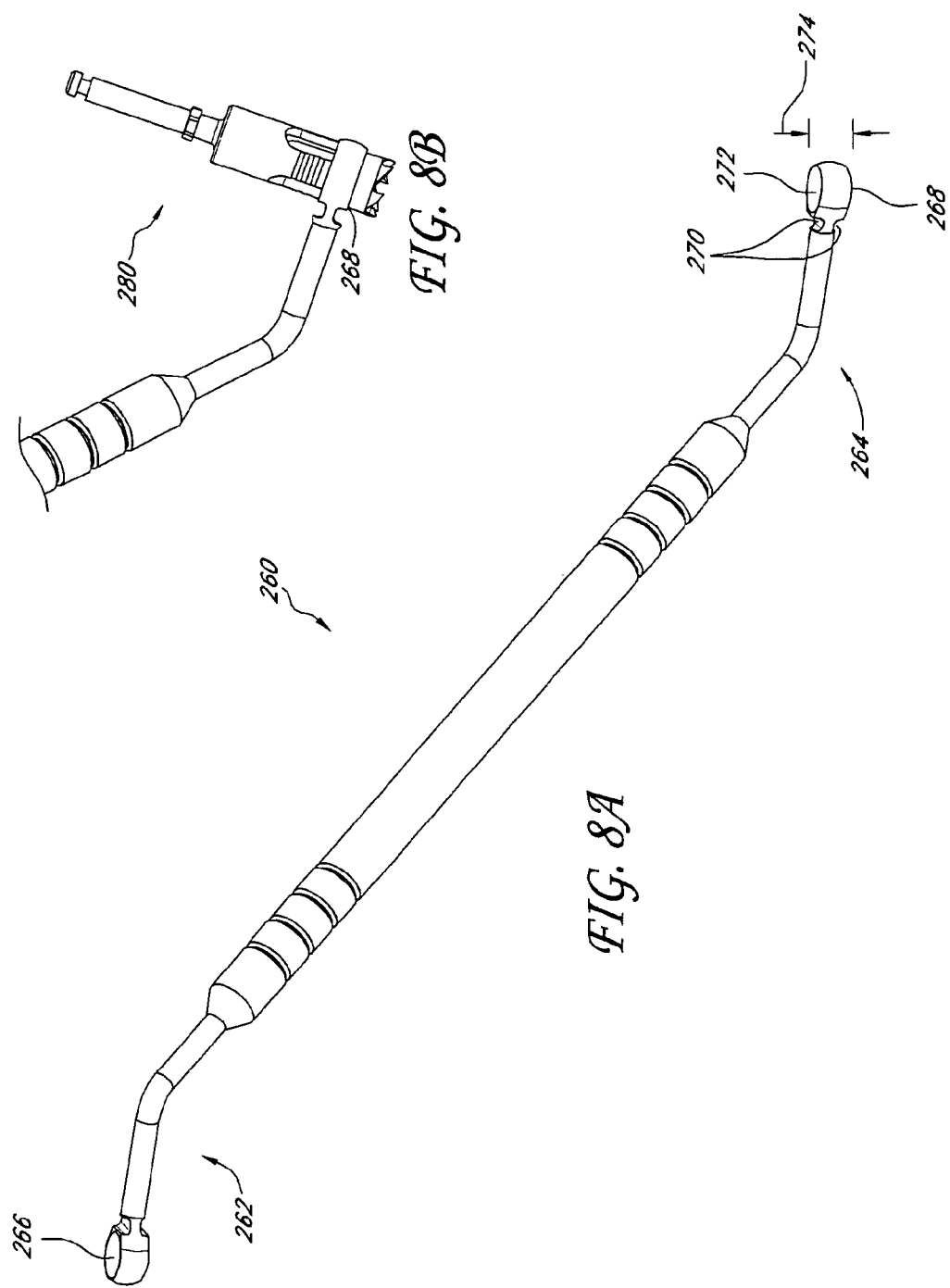

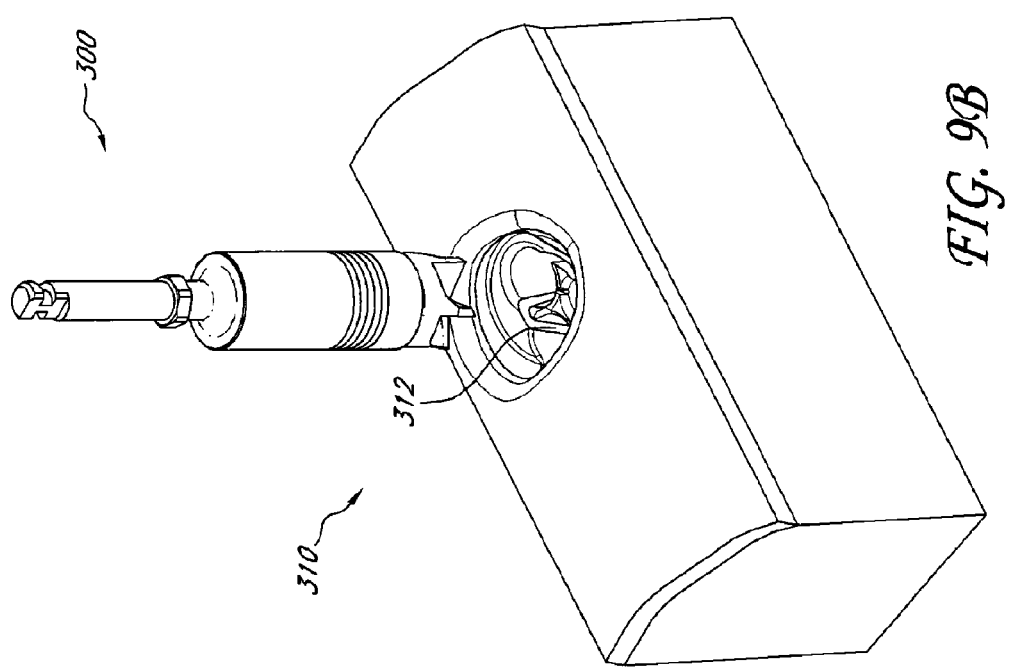

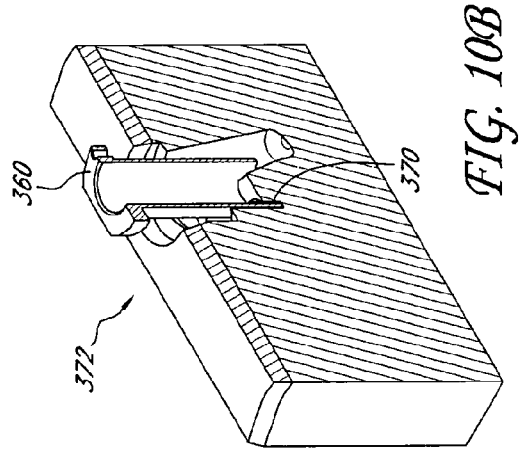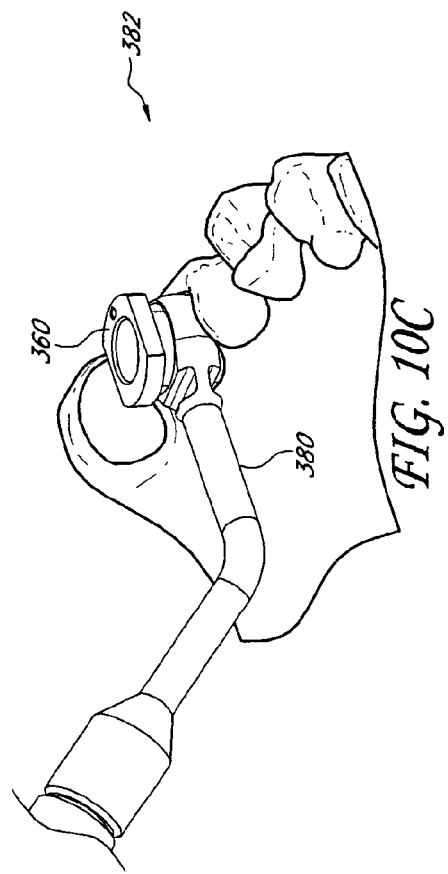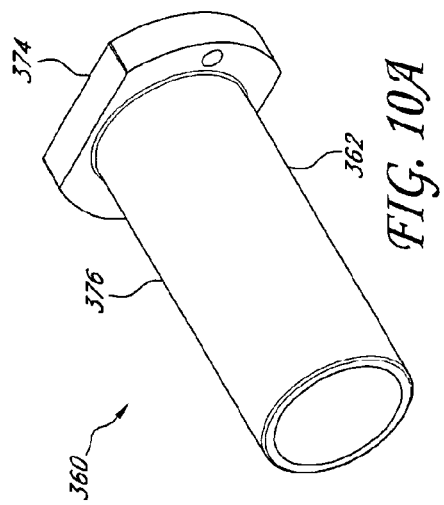

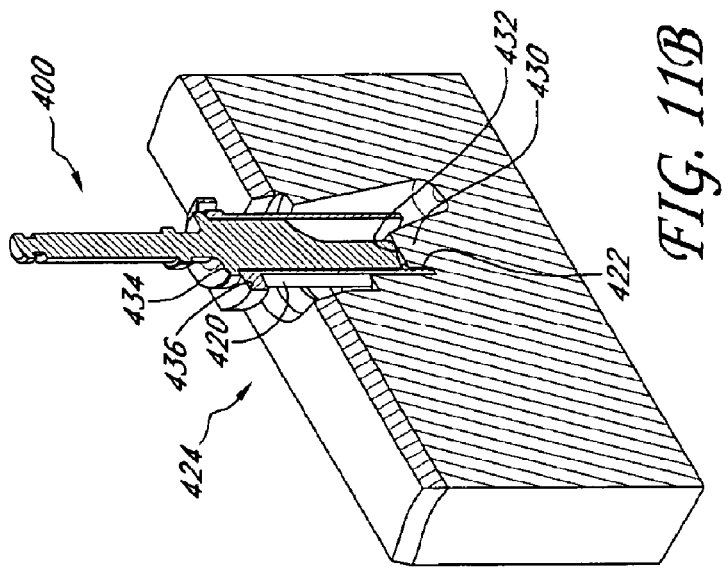
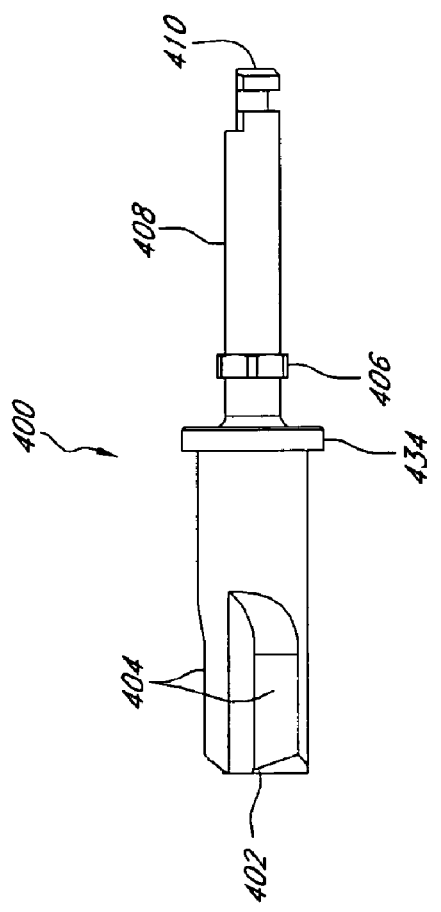

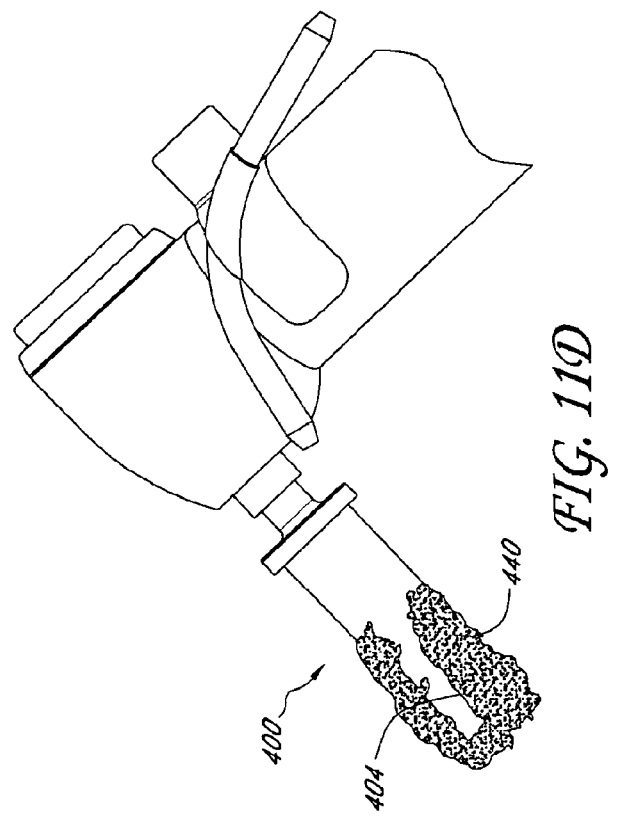
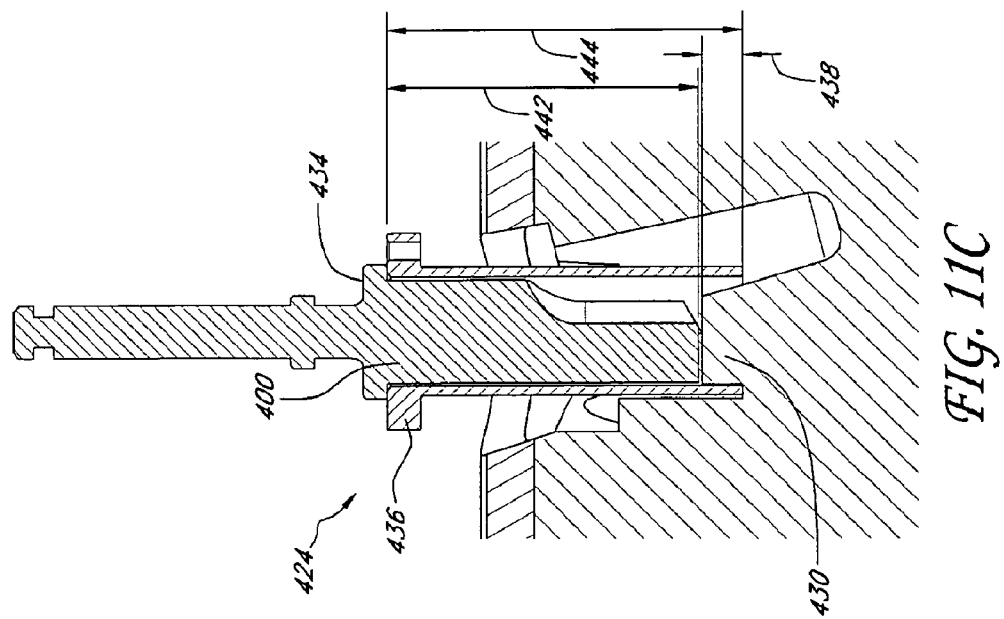
FIG. 11D
FIG. 11C

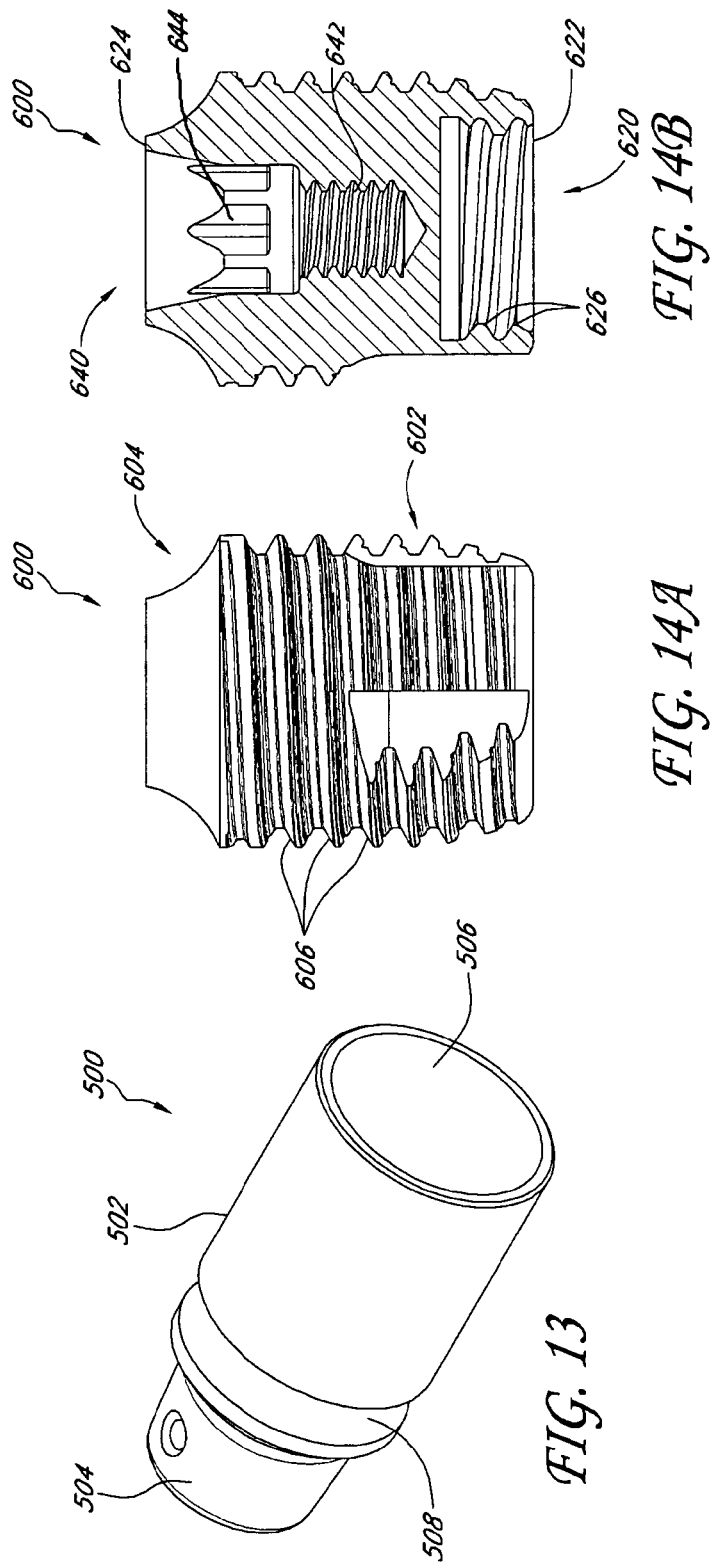

DEVICE AND PROCEDURE FOR IMPLANTING A DENTAL IMPLANT

PRIORITY APPLICATIONS

The present application is a continuation of U.S. patent application Ser. No. 13/260,252, filed Jan. 26, 2012, which is a U.S. National Phase of International Application No. PCT/EP2009/006535, filed Sep. 9, 2009, which claims the benefit of U.S. Provisional Application No. 61/095,923, filed Sep. 10, 2008. International Application No. PCT/EP2009/006535, filed Sep. 9, 2009 being hereby incorporated by reference herein in its entirety.

FIELD OF THE INVENTIONS

The present inventions relate generally to dental implant systems and methods of using the same. More specifically, the present inventions relate to methods and apparatuses for implant placement procedures and systems.

DESCRIPTION OF THE RELATED ART

Implant dentistry involves the restoration of one or more teeth in a patient's mouth using artificial components. Such artificial components typically include a dental implant and a prosthetic tooth and/or a final abutment that is secured to the dental implant.

The dental implant is implanted into the alveolar bone (i.e., jawbone) of a patient. Typically, the surgeon first accesses the alveolar bone through the patient's gum tissue and removes any remains of the tooth to be replaced. Next, the specific site in the alveolar bone where the implant will be anchored is prepared by drilling and/or reaming to accommodate the width of the dental implant to be inserted. Then, the dental implant is inserted into the hole, typically by screwing, although other techniques are known for introducing the implant in the jawbone.

As illustrated in FIGS. 1-3, a target site 10 for placement of an implant, such as an extraction site, can include several dental alveoli or tooth sockets 12. FIGS. 2-3 illustrate the placement in one of the sockets 12 of a prior art dental implant 14 having an angled abutment. This procedure is generally advantageous because it allows a surgeon to use the existing sockets 12 in order to place the implant 14, thus allowing the implant 14 to be placed relatively quickly.

FIG. 3 also illustrates that although the implant 14 can be placed into one of the sockets 12, a final restoration 16 installed onto the implant 14 will not be centered with respect to a centerline 18 of the target site 10. In other words, because the sockets 12 of such a site 10 are generally not centered relative to the centerline 18 of the site 10, the implant 14 will similarly be off-center. As a result, the final restoration 16 may be misaligned with respect to adjacent teeth and is cantilevered on the implant potentially adding additional stresses to the implant.

In contrast, an alternative procedure is to allow the extraction site where the tooth has been removed to heal prior to the implantation of a dental implant. For example, after removing the tooth, the sockets of the extraction site are sutured and further surgery is delayed until the bone heals to provide a "healed ridge." Depending on the tooth being replaced, such a procedure may be preferable. In fact, because the site is now healed, the surgeon can place the implant in any desirable orientation relative to the bone. However, allowing the site to heal can take up to several months which can be a burden on the patient.

Recently, threaded basket-type implants have been developed, which are particularly suited for implantation in the molar socket of the extraction site. For example, as described in U.S. Patent Publication 2005/0164146, to Cantor, a tubular anchoring element that can be inserted into a molar socket of the extraction site immediately after the tooth is removed. The molar socket is prepared by creating a hole that generally corresponds to the cervical collar of the socket. The hole is preferably configured such that it provides a large periphery of contact between the anchoring element and the cervical collar. Further, a flat surface can be prepared on the residual interradicular bone to support a portion of the anchoring element. Thus, the anchoring element can be implanted into the prepared molar socket. The prepared molar socket can provide good initial stability to the anchoring element and subsequent osseointegration allows the anchoring element to be further stabilized. I In a similar, as described in U.S. Patent Publication 2008/0003539, to Lundgren, a trephine drill can be used to prepare an implant site for receiving an anchoring element. The bone anchoring element comprises a threaded tubular implant that is coupled to a prosthetic component. The trephine drill is used to cut through connecting tissue, and an underlying thin bone layer is hacked or pressed to the bottom of the groove by means of a lifter. The tubular implant can then be inserted into the resulting hole.

SUMMARY

Despite the improvements made in the prior dental implants and dental implant procedures, there is still a need for improved procedures and devices for to ensure that dental implants are quickly reliably placed in the patient in a manner that consistently results in quick and proper osseointegration.

Accordingly, an aspect of at least one embodiment of the present inventions includes the realization that a dental implant procedure can be expedited if alternative tooling and procedures were utilized. An aspect of at least one of the embodiments disclosed herein is the realization that the use of an angled abutment causes a final restoration to be installed in an off-center orientation that misaligns the final restoration relative to the position of the original tooth and adjacent teeth.

Further, according to at least one of the embodiments disclosed herein is the realization that in preparing a target site to receive a dental implant, a central area or core of the target site may be used not only to anchor a straight implant, thereby eliminating the need to use an angled abutment and implant in order to correct the angle of an implant placed in a tooth socket, but can also provide valuable autogenous bone material that can be grafted into selected portions or cavities of the target site. In addition, the implant can be used at target sites such as, for example, where the bone height is lower. Bone height can be lower, for example, as a result of regression of the bone, or along the mandible or elsewhere where there is a low bridge ridge.

Another aspect of at least one embodiment of the present inventions includes the realization that a drill, such as a trephine drill, can be used to create a cylindrical osteotomy at the target site. The osteotomy can traverse one or more tooth sockets and extend into the bone toward a central area or core of the target site. As such, the resulting cylindrical osteotomy can create an interior bone cylinder or post that extends upwardly from a base of the target site.

One of the advantage of some of the embodiments disclosed herein is that a guide tool can be provided for assisting in the use of other tools, such as the trephine drill mentioned above and others such as a facing burr. The guide tool can be particularly advantageous because it can aid a surgeon in supporting a tool in a given orientation during use of the tool. As a result, the surgeon will tend to have greater control over the tool. Thus, the surgeon can be enabled to precisely place tools during procedures and improve cutting accuracy. Additionally, the improved control over the tools can facilitate safe handling of the tools.

For example, in some embodiments, it is particularly advantageous to use the guide tool with the trephine drill. The target site, as mentioned above, can often include several tooth sockets. Therefore, the portion of the target site that lies at the surface of the jawbone where the tooth sockets converge can often be defined by several sharp edges. Without the use of the guide tool, it can be particularly difficult to place the trephine drill in such a manner as to maintain a desired position and trajectory of the drill. During use, the trephine drill can sometimes be very unstable and wobble when it contacts the gum tissue and/or the bone. However, by using the guide tool, the surgeon can maintain a desired position even against sharp edges of varying heights. Further, the trajectory of the drill can also be precisely controlled, thus optimizing the osteotomy. Accordingly, the bone post created by the osteotomy can be formed precisely to a desired geometry.

In some embodiments, the bone post created by the osteotomy can be surrounded by a generally cylindrical cavity or wall of bone that is spaced from the bone post at a width defined by the width of the cylindrical drill. The bone post can be formed using a coring tool, such as an interradicular burr, which can be configured to collect bone material while preparing the bone post. The bone post and the cylindrical cavity can traverse portions of existing tooth sockets. However, the surfaces of the bone post and the cylindrical cavity can extend generally concentrically and provide sufficient support for engaging threads of a hollow lower portion of an implant. When installed, the implant can engage at least one of the bone post and the cylindrical cavity of the prepared site in order to anchor the implant at the target site and autogenous bone material can be grafted into the target site.

Accordingly, various embodiments disclosed herein also include the realization that a placement procedure can be developed in which after the target site is prepared and the implant is placed, bone tissue removed from the target site can be selectively grafted into the target site in order to fill cavities of the target site, such as empty tooth sockets and enhance the stability of the implant. For example, bone tissue collected during a reaming or coring process can be grafted into the target site and provide additional stability for the implant.

Furthermore, embodiments of the procedure and tools disclosed herein can provide a cutting tool that is configured to create a measured cut into the target site. For example, the tool, such as the interradicular burr mentioned above, can comprise a limit flange at a proximal end thereof that can be used to allow the surgeon to limit the longitudinal travel of the tool. In some embodiments, the flange can provide a visual indication to the surgeon. Further, in other embodiments, the flange can extend radially outwardly from the tool such that the flange limits the travel of the tool via interference. In other words, the shape of the flange can prevent or limit movement of the tool.

In accordance with an embodiment, a procedure is provided for implantation of an implant at a target site. The procedure can comprise the steps of: performing an osteotomy at the target site, the osteotomy defining a central bone post, a cavity wall, and an annular space intermediate the bone post and the cavity wall; collecting autogenous bone material from the target site; placing the implant at the target site; and grafting the autogenous bone material into selected portions of the target site.

The step of performing the osteotomy can comprise using a trephine drill. The step of performing the osteotomy can also comprise using a guide tool with the trephine drill for placing the trephine drill at the target site. The step of performing the osteotomy can further comprise using an angled guide tool.

The procedure can further comprise inserting a coring tool into the osteotomy to core the osteotomy. In this regard, the procedure can also further comprise coring the target site up to a depth less than the depth of the osteotomy. Further, the procedure can also comprise collecting autogenous bone material from the target site during coring of the osteotomy.

Additionally, the procedure can comprise placing a guide sleeve into the osteotomy. The step of inserting the coring tool can comprise inserting the coring tool into the guide sleeve. In some embodiments, the coring of the target site can comprise inserting the coring tool into the sleeve until a limit flange of the coring tool contacts a limit flange of the guide sleeve. The coring of the target site can also comprise coring the target site up to a depth being approximately 2 mm less than a depth of the osteotomy. The step of placing the guide sleeve can comprise inserting the guide sleeve through an aperture of a guide tool for placing the cylindrical sleeve into the osteotomy. The step of placing the guide sleeve can comprise using an angled guide tool.

The procedure can also comprise facing the target site with a facing burr after performing the osteotomy. "Facing" of the target site can comprise removing at least a portion of an upper surface of the target site in order to smooth out the target site. The facing operation can provide a smooth upper surface that facilitates proper seating of the implant. Further, the facing operation can also allow a surgeon to collect autogenous bone material. As described further herein, the facing operation can provide a generally flat upper surface that extends beyond a perimeter of an osteotomy at the target site. The step of facing the target site can comprise using a guide tool with the facing burr for placing the facing burr at the target site.

The step of grafting the autogenous bone material into the selected portions of the target site can comprise grafting the autogenous bone material into tooth sockets remaining after extraction of a tooth.

The procedure can further comprise inserting one of a plurality of try-in components into the osteotomy at the target site. The procedure can further comprise transferring a threaded pattern to the target site using a tapping tool.

In accordance with another embodiment, a procedure is provided for implantation of an implant at a target site. The procedure can comprise the steps of: making an osteotomy at the target site, the osteotomy extending from an upper surface of the target site into the bone toward a lower portion thereof, the osteotomy being made generally transversely relative to tooth sockets to define a bone post extending upwardly from the lower portion of the target site and a cavity wall adjacent to the bone post, the bone post being generally cylindrical, the cavity wall generally encircling the bone post and defining an annular space therebetween, the annular space being configured to receive a lower portion of the implant; placing a guide sleeve into the osteotomy; removing bone material from the bone post up to a depth less than the depth of the osteotomy; and placing the implant at the target site in the osteotomy with the lower portion thereof being received into the annular space of the osteotomy and an inner cavity of the implant receiving the bone post therein.

The procedure can further comprise grafting the bone material into selected portions of the target site. The procedure can also comprise inserting an interradicular bone coring tool into the guide sleeve for removing the bone material from the bone post.

The step of placing the guide sleeve can comprise inserting the guide sleeve through an aperture of a guide tool for placing the guide sleeve into the osteotomy. The step of placing the guide sleeve can comprise using an angled guide tool. The procedure can also comprise facing the target site with a facing burr after performing the osteotomy.

In accordance with another embodiment, a combination is provided for creating a prepared site for a dental implant. The prepared site can comprise an annular space and a bone posed defining a shelf. The combination can comprise a trephine drill and an interradicular burr. The trephine drill can define inner and outer diameters. The outer diameter of the trephine drill can be approximately equal to a minor diameter of external threads on the implant, and the inner diameter can be approximately equal to a major diameter of internal threads on the implant. The interradicular burr can define an outer diameter being less than the inner diameter of the trephine drill.

In some embodiments, the combination can further comprise a guide sleeve. The guide sleeve can define inner and outer diameters. The guide sleeve can be generally cylindrical. The outer diameter can be approximately equal to the outer diameter of the trephine drill, and the inner diameter can be approximately equal to the inner diameter of the trephine drill. The guide sleeve can be configured to removably receive the interradicular burr therein. The guide sleeve can comprise a limit flange at a proximal end thereof. The burr can comprise a limit flange at a proximal end thereof. Further, the burr can define an operational longitudinal length that is less than an effective longitudinal length of the guide sleeve.

The combination can further comprise an implant. The implant can define an outer diameter. In this regard, the outer diameter of the trephine drill can be approximately equal to the outer diameter of the implant.

Additionally, the interradicular burr can be configured to collect bone material. In this regard, the interradicular burr can have a plurality of flutes. The flutes can be configured to collect bone material during operation of the interradicular burr against the bone at the target site.

In accordance with some embodiments, the combination further comprises a guide tool defining at least one support structure formed at a distal end thereof. The support structure can define a receiving aperture having an inner geometry corresponding to the outer diameter of one of the trephine drill and the interradicular burr for supporting the respective one of the trephine drill and the interradicular burr. In some embodiments, the guide tool can comprise two support structures formed at opposing ends thereof. In this regard, the inner geometry of a first support structure can correspond to the outer diameter of the trephine drill and the inner geometry of a second support structure can correspond to the outer diameter of the interradicular burr.

Further, some embodiments of the combination can also comprise a tapping tool. The tapping tool can comprise a threaded surface for transferring a threaded pattern to the prepared site. In yet other embodiments, the combination can comprise at least one try-in component. The try-in component can define inner and outer diameters being approximately equal to the inner and outer diameters of the trephine drill.

In another embodiment, a combination is provided for performing an implantation of an implant at a target site. The combination can comprise a guide sleeve and an interradicular burr. The guide sleeve can define inner and outer diameters. The guide sleeve can also comprise a limit flange at a proximal end thereof. Further, the guide sleeve can define an effective longitudinal length. The interradicular burr can define an outer diameter that is less than the inner diameter of the guide sleeve such that the burr can be removably received within the guide sleeve. Additionally, the burr can define an operational longitudinal length that is less than the effective longitudinal length of the guide sleeve. The burr can comprise a corresponding limit flange configured to contact the limit flange of the guide sleeve when the burr is inserted into the guide sleeve. The corresponding limit flange of the burr can be configured to limit the longitudinal movement of the burr within the guide sleeve.

Additionally, the limit flange of the guide sleeve can be a generally circular planar flange. The limit flange of the burr can be a generally circular planar flange. Further, the interradicular burr can be configured to include a plurality of flutes for collecting bone material.

Some embodiments of the combination can be configured such that a longitudinal length of the interradicular burr is less than a longitudinal length of the guide sleeve. In other embodiments, longitudinal lengths of the burr and the guide sleeve can be configured such that a distal end of the burr is spaced approximately 2 mm from a distal end of the guide sleeve when the interradicular burr is inserted to within the guide sleeve. The combination can further comprise an implant having an outer diameter. The outer diameter of the implant can be approximately equal to the outer diameter of the guide sleeve.

The combination can also further comprise a trephine drill defining inner and outer diameters. The outer diameter of the trephine drill can be approximately equal to the outer diameter of the guide sleeve. The inner diameter of the trephine drill can be approximately equal to the outer diameter of the burr. In accordance with such embodiments, the combination further comprises a guide tool defining at least one support structure formed at a distal end thereof. The support structure can define a receiving aperture having an inner geometry corresponding to the outer diameter of one of the trephine drill and the interradicular burr for supporting the respective one of the trephine drill and the interradicular burr. In some embodiments, the guide tool can comprise two support structures formed at opposing ends thereof. In this regard, the inner geometry of a first support structure can correspond to the outer diameter of the trephine drill and the inner geometry of a second support structure can correspond to the outer diameter of the interradicular burr. In other embodiments, it is contemplated that the outer diameter of the trephine drill can be approximately equal to the outer diameter of the facing burr.

In yet another embodiment, the combination can comprise a guide tool defining at least one support structure formed at a distal end thereof. The support structure can define a receiving aperture having an inner geometry corresponding to the outer diameter of the interradicular burr for supporting the interradicular burr.

Further, some embodiments of the combination can also comprise a tapping tool. The tapping tool can comprise a threaded surface for transferring a threaded pattern to the prepared site. In yet other embodiments, the combination can comprise at least one try-in component. The try-in component can define inner and outer diameters being approximately equal to the inner and outer diameters of the trephine drill.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 5A is a cross-sectional perspective view of the prepared target site shown in FIG. 4 wherein a dental implant has been placed, according to an embodiment.

FIG. 6A is a perspective view of a trephine drill having a hollow bore, in accordance with an embodiment.

FIG. 6B is a cross-sectional side view of the trephine drill of FIG. 6A.

FIG. 6C is a perspective view of a target site after the application of the trephine drill, according to an embodiment.

FIG. 7A is a perspective view of a trephine drill comprising a burr component, in accordance with an embodiment.

FIG. 7B is a cross-sectional side view of the trephine drill of FIG. 7A.

FIG. 8A is a perspective view and an enlarged view of a guide tool in accordance with an embodiment.

FIG. 8B is a perspective view of the guide tool of FIG. 8A supporting the trephine drill, according to an embodiment.

FIG. 9B is a perspective view of a target site after the application of the facing burr, according to an embodiment.

FIG. 10A is a perspective view of a guide sleeve in accordance with an embodiment.

FIG. 10B is a cross-sectional perspective view of the sleeve of FIG. 10A being placed into a target site, according to an embodiment.

FIG. 10C is a perspective view of a sleeve of FIG. 10A being placed at a target site using a guide tool, according to an embodiment.

FIG. 11A is a perspective view of an interradicular burr in accordance with body an embodiment.

FIG. 11B is a cross-sectional perspective view of a target site during the application of the interradicular burr, according to an embodiment.

FIG. 11C is a cross-sectional side view of a target site illustrating the application of an interradicular burr and a guide sleeve, according to an embodiment.

FIG. 11D is a perspective view of an interradicular burr subsequent to use and illustrating collection of bone material in flutes of the burr, according to an embodiment.

FIG. 13 is a perspective view of a try-in component in accordance with an embodiment.

FIG. 14A is a perspective view of an implant in accordance with an embodiment.

FIG. 14B is a cross-sectional side view of the implant of FIG. 14A.

DETAILED DESCRIPTION OF THE PREFERRED EMBODIMENTS

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein.

As discussed above, previous implantation procedures have various disadvantages. For example, when a tooth is extracted and replaced with an implant, a surgeon would have to utilize existing tooth sockets in order to perform such a procedure within a short time frame. Unfortunately, in order to perform such a procedure, an implant would require that an angled abutment be used in addition to the implant in order to compensate for the off-axis geometries of the tooth sockets. As noted above, the use of an angled abutment results in an off-center final restoration. In another example, a surgeon may be entirely unable to use existing tooth sockets of an extraction site. Therefore, the surgeon would have to allow the extraction site to heal completely, thus producing a healed ridge. Such a procedure could require several additional months before an implant could be placed.

In accordance with at least one of the embodiments disclosed herein, an implant placement procedure is provided that enables a surgeon to place an implant directly into a target site in a generally vertical orientation, thereby eliminating the need for angled abutments and implants as well as the need for significant periods of time between steps in the procedure. In particular, some embodiments provide for an implant placement procedure in which a target site is prepared by creating a hollow and generally cylindrical osteotomy at the target site. The osteotomy can be formed to provide several surfaces that can be engaged by a dental implant in order to securely install the implant at the target site.

Figure 4:
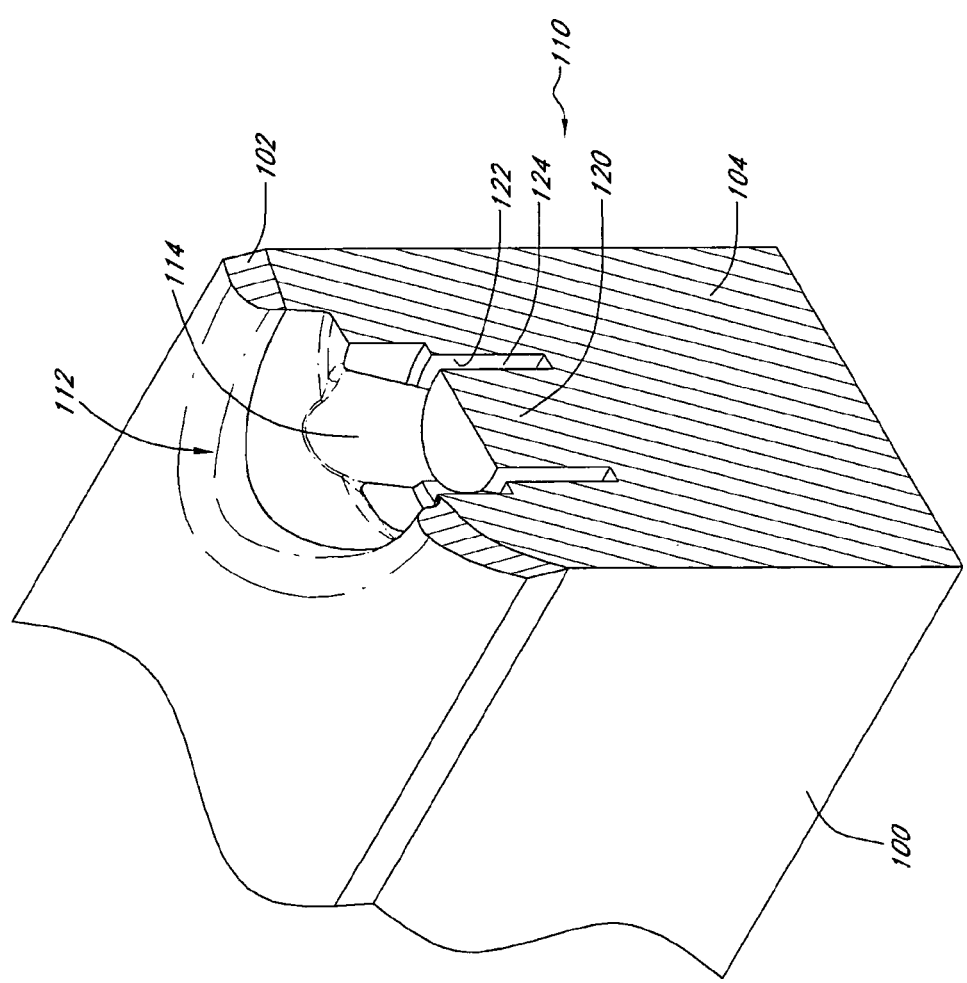
FIG. 4 is a cross-sectional perspective view of a prepared target site, in accordance with an embodiment of the present inventions.

FIG. 4 is a cross-sectional perspective view taken along a mandible or jawbone 100 of a patient. The jawbone 100 comprises a layer of gum tissue 102 and bone tissue 104. The view shown in FIG. 4 illustrates the configuration of a finished or prepared site 110 according to one embodiment. As described herein, the prepared site 110 is formed at a target or implant site 112. The target site 112 can be used for implanting a dental implant or tooth replacement for any tooth, such as an incisor, a canine, a bicuspid, or a molar. In some embodiments, the target site 112 can be a fresh extraction site from which a tooth has been removed, a molar extraction site, a healed ridge or healed extraction site, or other site along the dental cavity (e.g., a site that a result of regression of the bone, or along the mandible or elsewhere where there is a low bridge ridge). As such, the target site can comprise one or more dental alveoli or tooth sockets 114. For example, after a tooth has been removed, the tooth sockets 114 generally remain exposed. In the figures used to illustrate certain embodiments, the tooth is shown as being a molar, and the target site is an extraction site.

As noted above, some implantation procedures may utilize existing tooth sockets in order to place the implant. However, as discussed herein, embodiments of the present inventions enable a surgeon to prepare a target site and install an implant regardless of the configuration of the target site, whether the target site includes existing tooth sockets, a healed ridge or otherwise configured dental geometry. Further, embodiments also enable a surgeon to perform in implant procedure in a single day. Finally, embodiments disclosed herein also provide for an implant that is more securely retained in the jawbone due to the unique structure of the implant. Therefore, it should be appreciate that embodiments of the procedures and instruments described herein can be used in an extraction site, a molar extraction site, a healed ridge, or a site without tooth sockets.

The prepared site 110 shown in FIG. 4 includes a central bone post 120, a cylinder cavity or wall 122, and an annular space 124 formed between the bone post 120 and the cavity 122. The annular space 124 can extend to a desirable depth into the bone 104 of the jawbone 100. As will be appreciated by one of skill in the art, the configuration of any tooth sockets 114 and the size of the target site 112 provide important factors for determining not only the depth of the annular space 124, but also the diameter of the space 124.

For example, it is contemplated that when replacing a molar, a target site or an extraction site might be between 10-12 mm in diameter. However, the dimensions of the target site or the extraction site, including the depth and angular orientation of tooth sockets will vary depending on the individual. Therefore, great care should be taken in ensuring that the annular space 124 is suitable for a given implant and jawbone.

FIG. 5A is a cross-sectional perspective view of the jawbone 100 shown in FIG. 4. However, FIG. 5A also illustrates an implant 140 that is placed at the prepared site 120. As illustrated therein, the implant 140 comprises a lower portion 142 that is hollow and generally cylindrical. The lower portion 142 also comprises an exterior surface having a plurality of exterior threads 144 and interior cavity having a plurality of interior threads 146. Nevertheless, in other embodiments, the implant 140 can also comprise a lower portion 142 that is solid. Such an embodiment may be useful for implant sites in which less room is available and/or the depth of the implant must be limited, such as with a shorter tooth socket(s).

The "pitch" of a screw thread is generally defined as the distance from one thread groove to the next measured axially. "Lead" is generally defined as the distance a screw thread advances in one revolution. "Start" is a term that generally refers to the number of independent screw threads on a screw member. The "lead" of a screw member is equal to the pitch of the screw member multiplied by the number of starts on the screw member. In an embodiment, the interior and exterior threads 146, 144 have the same pitch and preferably have the same lead. In accordance with another embodiment, the interior threads 146 can have double or quadruple starts while the exterior threads 144 have a single start. Further, in another embodiment, the exterior threads 144 can have double or quadruple starts while the internal threads 146 have a single start. Finally, it is contemplated that the internal and exterior threads 146, 144 can both comprise double or quadruple starts. In another embodiment, one or both of the interior and exterior threads 146, 144 can be replaced with annular grooves, ridges, roughed or textured surfaces.

As illustrated in FIG. 5A, the interior threads 146 of the implant 140 are configured to engage the bone post 120 of the prepared site 110. Similarly, the exterior threads 144 of the implant 140 are configured to engage the cavity or wall 122 of the prepared site 110. Thus, the implant 140 can be securely retained within the annular space 124 of the prepared site 110. Additionally, osseointegration of the bone 104 about and within the implant 140 will provide further stabilization and engagement between the implant 140 and the jawbone 100.

Figure 1:
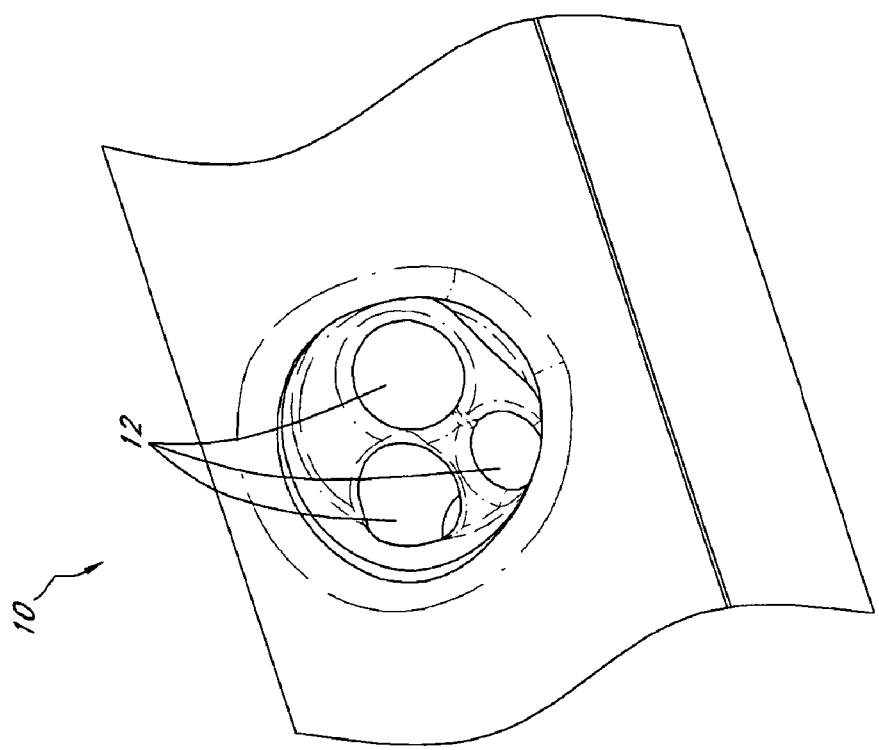
FIG. 1 is a perspective view of a target site of a jawbone from which a tooth, such as a molar, has been extracted.
Figure 2:
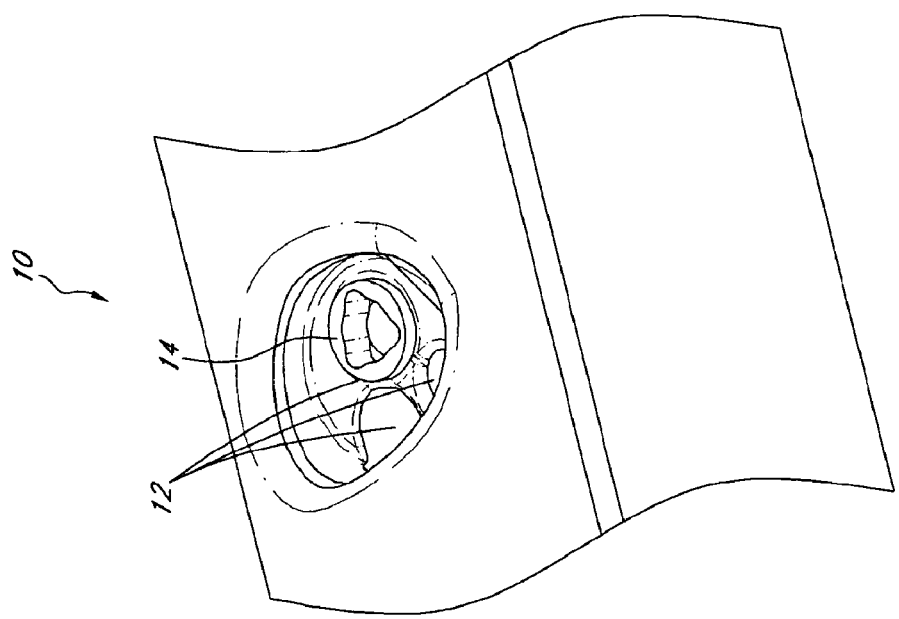
FIG. 2 is a perspective view of the target site shown in FIG. 1 in which a dental implant has been installed in a socket of the target site.
Figure 3:
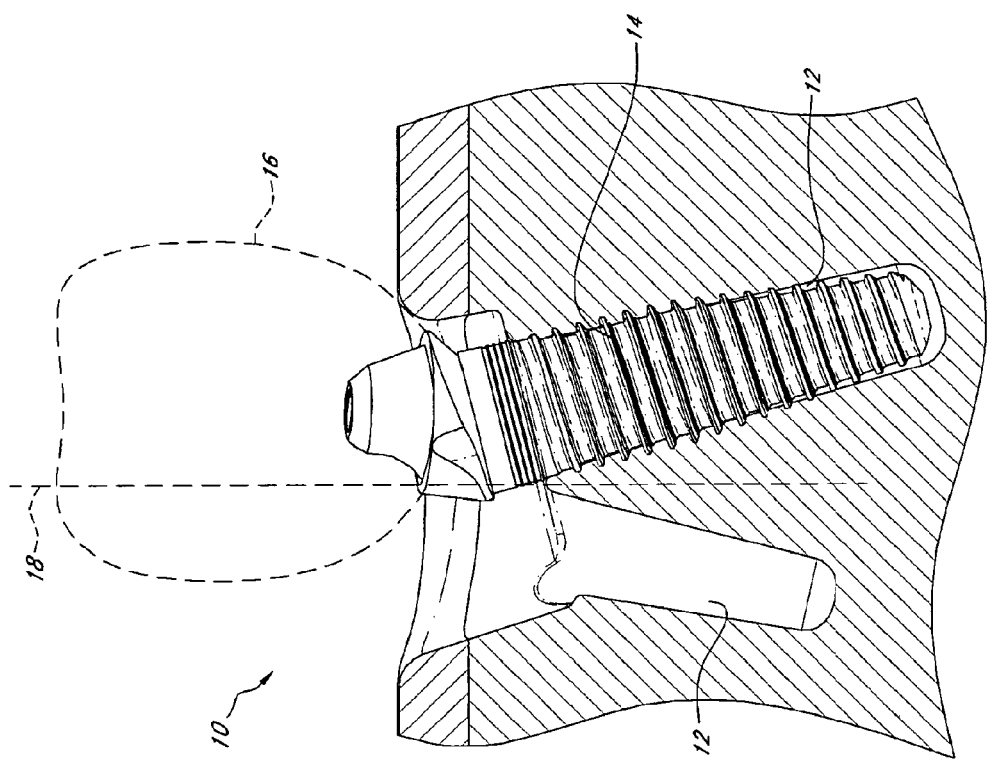
FIG. 3 is a cross-sectional side view of the target site and implant shown in FIG. 2, wherein the implant includes an angled abutment.
Figure 5B:
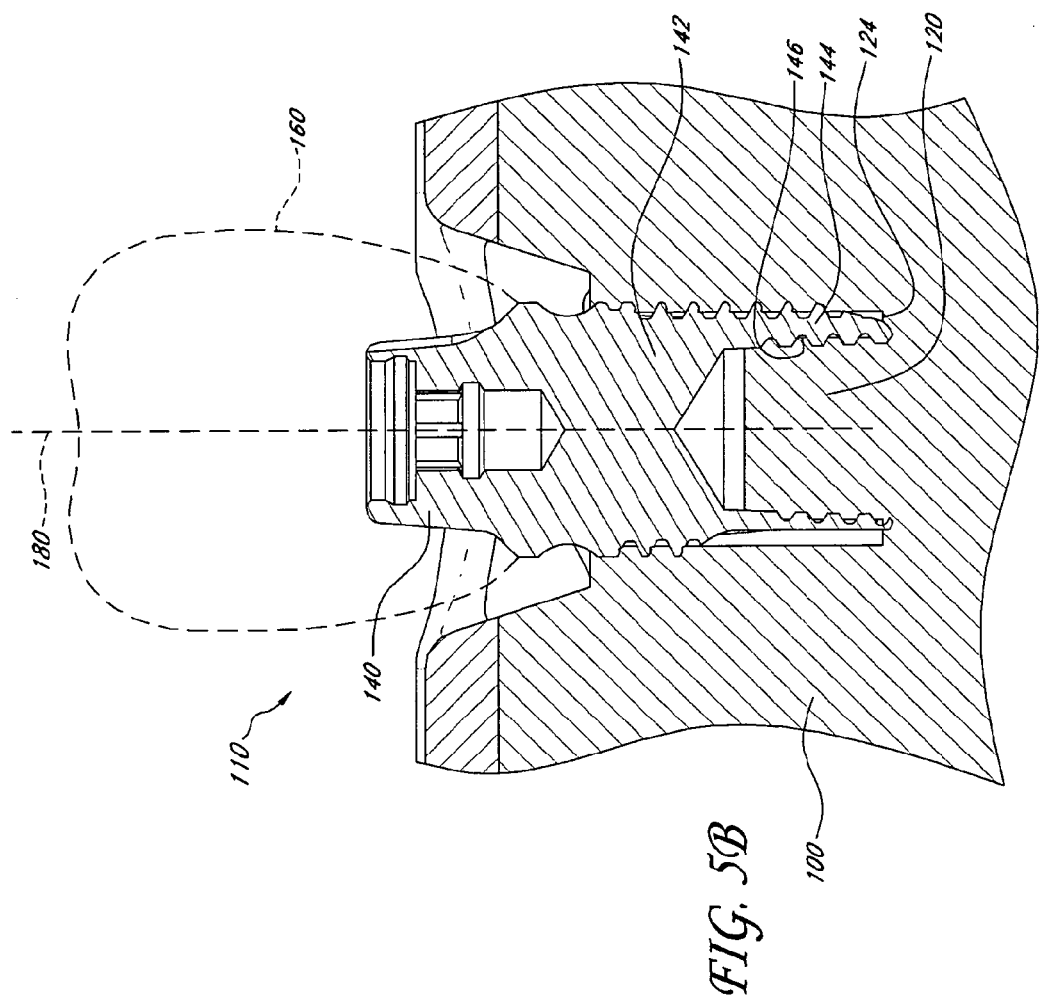
FIG. 5B is a cross-sectional side view of the prepared target site shown in FIG. 4 wherein the dental implant and a final restoration have been placed, according to an embodiment.

FIG. 5B illustrates a cross-sectional side view of the jawbone 100 and the implant 140 illustrated in FIG. 5B. However, FIG. 5B also illustrates a final restoration 160 that is installed on the implant 140. One of the innovative features of embodiments disclosed herein provides that the implant 140 can be generally centered relative to a centerline 180 of the prepared site 110. In this regard, the final restoration 160 will tend to be in an alignment similar to the original tooth that is centered and spaced natural relative to adjacent teeth. Thus, unlike an angled abutment that would otherwise be installed in a socket 114 and contribute to an off-centered final restoration as shown in FIG. 3, embodiments of the implant 140 allow the final restoration to be centered with respect to a centerline 180 of the site 110. Thus, the final restoration 160 will tend to be aesthetically superior to the previous final restoration 16 shown in FIG. 3.

With reference now to FIGS. 6A-14, methods and tools for preparing the prepared site 110 will now be described in greater detail. FIG. 6A is a perspective view of a trephine drill 200 for creating an osteotomy at the target site. The trephine drill 200 has a cylindrically-shaped tubular body 202 with a plurality of teeth 204 at a distal end 206 thereof. The drill 200 can also include a plurality of depth markers 208 for aiding the surgeon in achieving a desired depth of the osteotomy. The body 202 of the drill 200 can also be formed to a desired length. As shown in FIG. 6B, which is a cross-sectional side view of FIG. 6A, the drill 200 can comprise a body 202 having a hollow bore 209. In some embodiments, the length of the body 202 of the drill 200 can be approximately 5 mm.

Further, the drill 200 can define an inner and outer diameter that produces a circular cut in bone. In use, a surgeon can select a drill having desired inner and outer diameters based on the geometry of the target site. For example, the inner and outer diameters of the various embodiments of drills disclosed herein can correspond to the dimensions of tools and/or to an implant, as discussed herein. As discussed below, the inner and outer diameters can be approximately equal to the outer minor diameter of the threads on the implant and the inner diameter of the drill 200 is approximately equal to the inner minor diameter of the threads on the implant. In this regard, a "minor" diameter can be defined as the diameter of an imaginary coaxial cylinder that just touches the roots of an external thread or the crests of an internal thread. In this manner, the drill preserves bone material for engaging the threads. In other embodiments, the inner diameter of the drill 200 can be approximately greater than to the inner minor diameter of the implant and the outer diameter of the drill 200 can be approximately less than the outer major diameter of the implant. In this regard, a "major" diameter can be defined as the diameter of an imaginary coaxial cylinder that just touches the roots of an internal thread or the crests of an external thread.

As noted above with respect to U.S. Patent Application Publication No. 2008/0003539, a trephine drill can be used in oral surgery to prepare an extraction site. Therefore, in accordance with an aspect of at least one of the embodiments herein, the trephine drill 200 can be used for creating an osteotoemy. In particular, the drill 200 can be used to create an implantation space that extends into the bone of the jaw and traverses one or more of the existing tooth sockets. In this manner, the implantation space can define a sufficiently large surface area along which a dental implant can be engaged, such as by threaded engagement or otherwise. However, it is contemplated that other equipment can be used in preparing the target site and creating an osteotomy having a shape other than circular or cylindrical. For example, it is contemplated that an osteotome can also be used to prepare the target site. An osteotome can be used to improve the bone quality, such as by compaction of local bone, and bone quantity, by ridge extension in horizontal and vertical dimension. The osteotome can thus improve these aspects of the bone in order to enhance the stability of an implant.

For example, as shown in FIG. 6C, the drill 200 can be used at an target site 220. After the site 220 has been cleaned, the drill 200 can be placed with an axis of the drill 200 being aligned generally vertical or normal relative to the jawbone. The osteotomy should be done to a desired depth. For example, the surgeon can use the depth markers 208 in assessing the depth of the osteotomy.

In some embodiments, the drill 200 can be modified to comprise one or more torque transmitting sections 210 disposed along a shaft 212 of the drill 200 which can be engaged, along with a proximal engagement section 214, by a turning instrument in order to rotate the drill 200. The torque transmitting section 210 can be formed as a hex or other geometric shape configured to provide secure engagement and transfer of torque between a turning instrument and the drill 200. Further, the use of the torque transmitting section 210 can ensure that the shaft 212 of the drill 200 does not jam in the turning instrument, which may commonly occur if only the proximal engagement section 214 is used due to the significant torque that is exerted on the proximal engagement section 214.

Furthermore, as shown in FIG. 7A, some embodiments provide for a trephine drill 240 that can be configured to include a facing burr or burr component 242 disposed in a hollow bore 244 of the drill 240. A cutting edge 246 of the facing burr 242 can be longitudinally spaced from a distal end 248 of the drill 240 at a given distance 250. The distal end 248 of the drill 240 can be defined generally by the teeth thereof.

Therefore, the drill 240 can be configured such that in use, the distance 250 defines a height of a bone post upon cutting the interradicular bone at the target site. Further, the trephine drill 240 can be used not only to create the bone post, but can also create an annular space at the target site in a single pass. In embodiments of the procedures described herein, the use of the drill 240 could result in multiple steps of the procedure being combined into a single step, thus simplifying the procedure and shortening the operation time. However, it is contemplated that in other embodiments such a combination drill may also be separated into a trephine drill and an interradicular burr or coring tool as described further herein. The performance of the steps individually may allow a surgeon to precisely control and respond to operational conditions.

In an embodiment, the drill 240 can have inner and outer diameters 252, 254 that generally correspond to the dimensions of the implant that will be used. Similar to the drill 200 discussed above, in an embodiment wherein an implant comprises inner and outer threads, the outer diameter 254 of the drill 240 can be approximately equal to the outer minor diameter of the threads on the implant and the inner diameter 252 of the drill 240 is approximately equal to the inner minor diameter of the threads on the implant. In other embodiments, the inner diameter 252 of the drill 240 can be approximately greater than the inner minor diameter of the implant and the outer diameter 254 of the drill 240 can be approximately less than the outer major diameter of the implant.

Additionally, the inner and outer diameters of the drill 240 can correspond to a guide sleeve described further herein. The inner and outer diameters of the drill 240 can also correspond to a try-in component, which is also described further herein. In some embodiments, the inner and outer diameters of the drill 240 can be selected in order allow the drill 240 to create an annular space within the bone in order to allow one or more of a guide sleeve, a try-in component, and a tubular implant to be received therein.

In some embodiments of the procedure, a guide tool 260 can be used. An embodiment of the guide tool 260 is shown in FIGS. 8A-B. The tool 260 can be used in a variety of orientations during a procedure. The guide tool 260 is illustrated as an elongate shaft having first and second ends 262, 264 at which one or more respective support elements 266, 268 are placed. The length of the elongate shaft of the tool 260 can be modified as required. However, it is contemplated that the length may be between approximately 150 mm and approximately 200 mm. More specifically, the length of the shaft can be between approximately 165 mm and approximately 189 mm.

As mentioned above, one of the advantages of some of the embodiments disclosed herein is that the guide tool 260 can be used to assist in the placement and use of other tools, such as the trephine drill and the facing burr. The guide tool 260 can be particularly advantageous because it can allow a surgeon to have greater control of and precisely support a tool in a given orientation during use of the tool. Thus, the surgeon can be enabled to precisely place tools during procedures, improve cutting accuracy, and more safely handle the tools.

In some embodiments, the guide tool 260 can be part of a surgical template. For example, a surgical template such as in the Applicant's NobelGuide™ system can be used. Such surgical templates are described in U.S. Patent Application Publication Nos. 2004/0259051, filed on Jun. 23, 2004, 2007/0281270, filed on Jul. 4, 2005, 2006/0006561, filed on Jun. 30, 2005, and 2008/0118895, filed on Jul. 4, 2005, U.S. patent application Ser. No. 11/916,262, filed on Nov. 30, 2007, as well as International Patent Application Nos. PCT/SE02/02393, filed on Dec. 19, 2002, PCT/SE2005/001074, filed Jul. 4, 2005, the entireties of which are incorporated herein by reference.

In accordance with an embodiment, the first and second ends 262, 264 can be angled. The angular orientation of the first and second ends 262, 264 can be different in order to allow a surgeon flexibility in using the tool 260 depending on local geometries of the buccal cavity of the patient. The first and second ends 262, 264 can be oriented at angles ranging from approximately 0° to approximately 50°. In the illustrated embodiment, the angle is approximately 40°.

In some embodiments, the support elements 266, 268 can be formed as continuous annular structures having a given inner diameter. However, the support elements 266, 268 can also define a discontinuous perimeter or be formed in a shape other than annular. The support elements 266, 268 can define respective receiving apertures having interior geometries that are configured to receive at least one tool. For example, the inner diameters of the support elements 266, 268 can correspond to an outside diameter of a tool used in an embodiment of the implant procedures described herein for allowing the tool to be received by the support element. In an embodiment, the inner diameter of the support element 266 at one end can be different from the inner diameter of the other support element 268 at the other, opposite, end. In this manner, the tool 260 can be selectively configured to be used with more than one tool. The support element can engage the tool in such a manner that allows the tool to spin relative to the support element while allowing a surgeon to more precisely manipulate the position and orientation of the tool using the guide tool.

In some embodiments, the first and second ends 262, 264 can comprise one or more support grooves 270 disposed adjacent to the support elements 266, 268. The grooves 270 can be configured to allow the first and second ends 262, 264 to be more easily accommodated at the target site. Further, the grooves 270 can be disposed along the top and bottom portions of the first and second ends 262, 264 for flexibility of use in various orientations.

Additionally, as shown in FIG. 8A, the support elements 266, 268 can define a guide surface 272 having a height 274. Thus, in some embodiments, the guide surface 272 can be a generally cylindrical surface. The guide surface 274 can therefore restrict degrees of freedom of movement between the guide tool 260 and a tool being engaged by the guide tool 260.

For example, as shown in FIG. 8B, the support element 268 of the guide tool 260 can be configured to support a trephine drill 280 during performance of the procedure. Due to the cylindrical fitting between the guide tool 260 and the drill 280, only relative rotational movement along a longitudinal axis of the drill 280 and longitudinal sliding movement will be possible between the tool 260 and the drill 280, thereby allowing the tool 260 to control longitudinal and rotational movement of the drill 280 along axes transverse to the longitudinal axis of the drill 280. Thus, a surgeon can use both the tool 260 and the drill 280 to accurately place the drill 280 at the target site.

The use of the guide tool 260 can be especially advantageous when the trephine drill 280 is used at a target site having several tooth sockets. The portion of the target site that lies at the surface of the jawbone where the tooth sockets converge can often be defined by several sharp edges. As such, without the use of the guide tool 260, it can be particularly difficult to place the trephine drill 280 in such a manner as to maintain a desired position and trajectory of the drill 280. During use, the trephine drill 280 can sometimes be very unstable and wobble when it contacts the gum tissue and/or the bone. Such difficulties may also be present when using other tools as well. However, by using the guide tool 260, the surgeon can maintain a desired position even against sharp edges of varying heights. Further, the trajectory of the drill 280 can also be precisely controlled, thus optimizing the osteotomy.

Accordingly, it is contemplated that various components and dimensions of the guide tool 260 can be selectively modified so that the guide tool 260 can be used with tools of differing shapes and sizes. For example, a single guide tool can correspond to two trephine drills of different outer diameters. Further, the guide tool could correspond to a single diameter drill, but provide different angular orientations of support elements at the first and second ends of the guide. This versatility of the guide tool can allow a surgeon, if using the guide tool, to achieve a greater degree of precision and accuracy in using tools during the performance of a procedure.

In other embodiments of the procedure, a facing burr 300 can optionally be used to prepare the target site. In other words, the facing burr 300 can be used prior to the use of the trephine drill 200 in order to provide a smooth and/or flat surface against which the trephine drill 200 can be applied. Accordingly, the smooth and/or flat surface can aid the surgeon in aligning the trephine drill 200 such that the osteotomy can be properly centered and oriented in a desired manner.

Figure 9A:
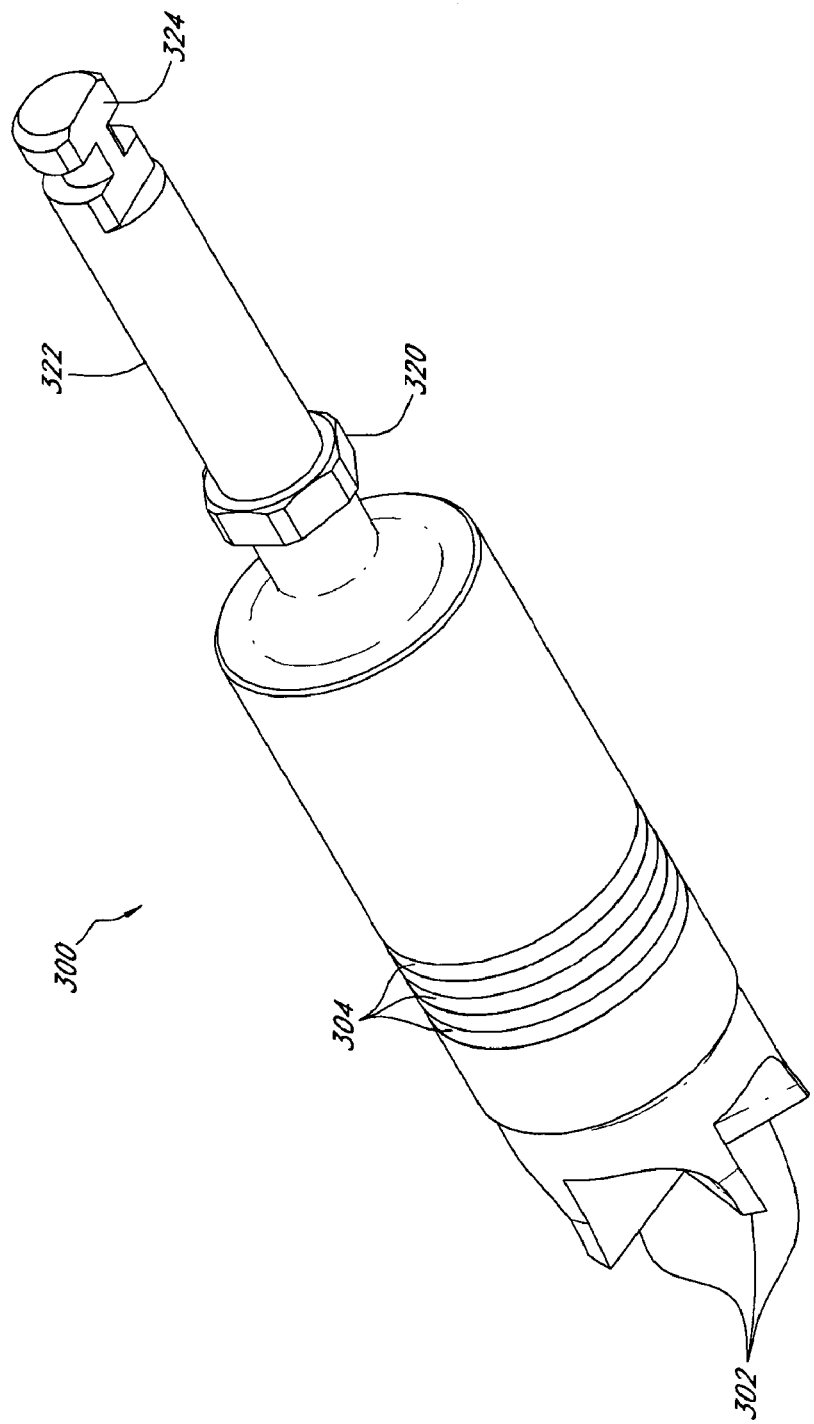
FIG. 9A is a perspective view of a facing burr in accordance with an embodiment.

Thus, the facing burr 300, such as shown in FIG. 9A, can be used to create a smooth and/or flat upper surface at the target site. Further, in some embodiments, the diameter of the facing burr 300 can be equal to the diameter of the trephine drill 200, as discussed above. However, it is also contemplated that the diameter of the facing burr 300 can be larger than the diameter of the trephine drill 200. Thus, in some embodiments, the burr 300 can prepare the target site to have a generally flat and smooth upper surface that extends circumferentially around the osteotomy created by the trephine drill 200.

Further, the facing burr 300 can be configured to include a plurality of depth markers 304. In use, the depth markers 304 can be monitored by the surgeon in order to allow the surgeon to be aware of and control the depth of the cut.

As discussed herein, the target site can be a tooth or molar extraction site. Accordingly, in some embodiments, it may be advantageous to smooth an upper surface of the target site. However, it is also contemplated that the upper surface at the target site may already be sufficiently smooth or it may be unnecessary to smooth out the upper surface. Therefore, the use of the facing burr 300 is optional in certain embodiments. As noted above, if the facing burr 300 is used, the facing procedure can be performed before the trephine drill or other tool has been used to create the osteotomy.

In embodiments of the procedure that utilize the facing burr 300, blades 302 of the facing burr 300 can be placed at a target site 310 as shown in FIG. 9B. The burr 300 rotates such that the blades 302 cut into the target site 310 to produce a smooth upper surface 312.

In some embodiments, the facing burr 300 can be used with a guide tool, such as the guide tool 260 described above. As such, a surgeon can more precisely place the burr 300 during the facing procedure. In particular, in one embodiment, a support member 266 of the guide tool 260 is configured to slideably receive the trephine drill 280 while the other support member 264 is configured to slideably receive the facing burr 300. In such a configuration, the guide surfaces 272 of the support members 266 preferably have an inside diameter that is slightly larger than the outside diameter of the corresponding tool.

The burr 300 can also comprise one or more torque transmitting sections 320 disposed along a shaft 322 of the burr 300 which can be engaged, along with a proximal engagement section 324, by a turning instrument in order to rotate the burr 300. The torque transmitting section 320 can be formed as a hex or other geometric shape configured to provide secure engagement and transfer of torque between a turning instrument and the burr 300. Further, the use of the torque transmitting section 320 can ensure that the shaft 322 of the burr 300 does not jam in the turning instrument, which may commonly occur if only the proximal engagement section 324 is used due to the significant torque that is exerted on the proximal engagement section 324.

Figure 9C:
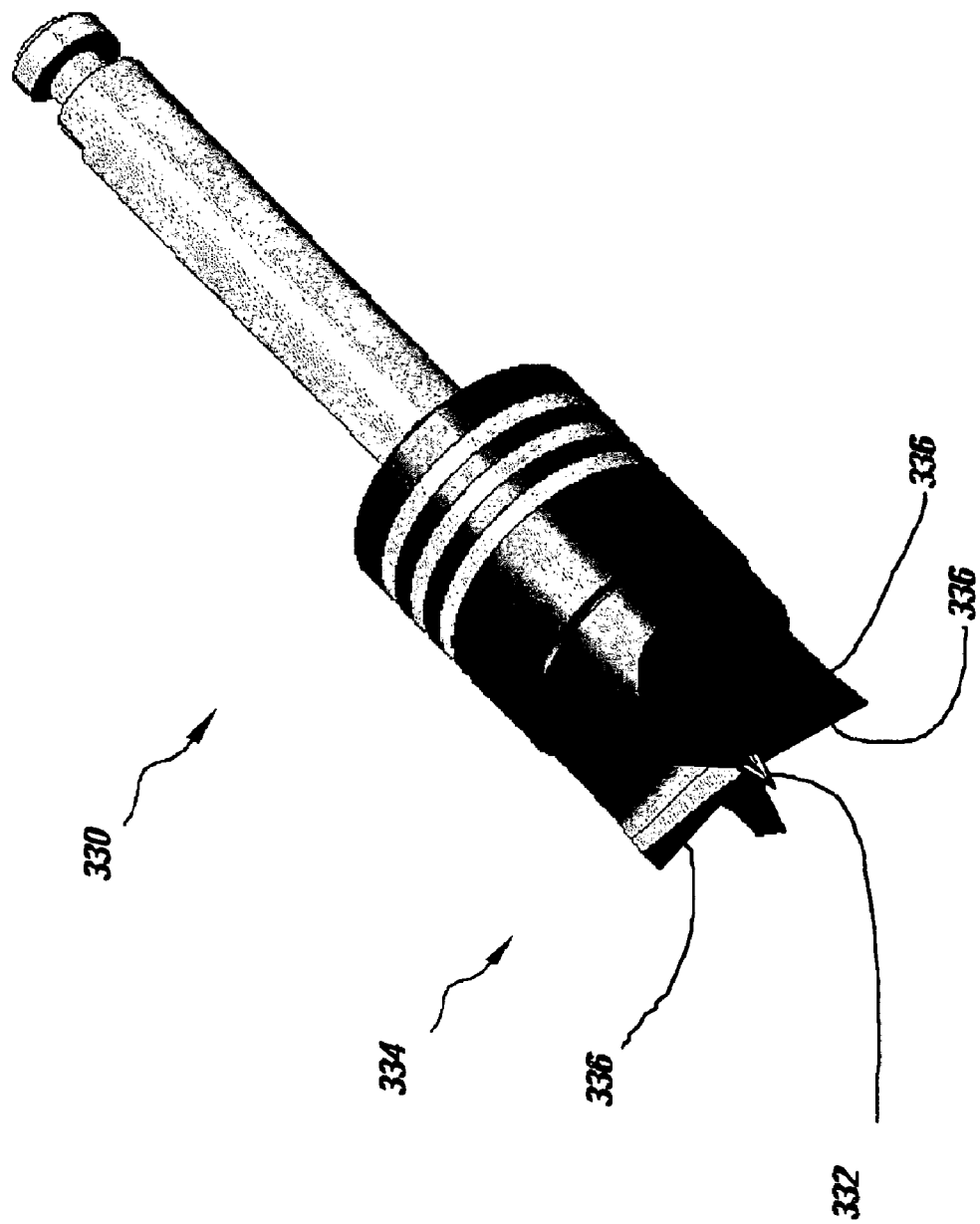
FIG. 9C is a perspective view of a facing burr in accordance with another embodiment.

FIG. 9C illustrated another embodiment of a facing burr 330. The facing burr 330 can comprise at least some of the features discussed above with respect to the facing burr 300. However, in addition, the facing burr 330 can also comprise a tip 332 disposed at a distal end 334 of the facing burr 330. In this regard, as shown in FIG. 9C, the tip 332 can extend from one or more blades 336 of the burr 330. The tip 332 of some embodiments of the facing burr can facilitate centering of the facing burr during use. For example, when the facing burr is being used to prepare an uneven surface, it may be difficult to center and maintain level or even the face or plane of the blades 336. Accordingly, the centering function of the tip 332 can enable a surgeon to reliably prepare the target site to a level and even surface. In particular, the tip can be especially useful when preparing a healed site. Otherwise, it is possible that the facing burr may move during use.

Referring now to FIGS. 10A-C, embodiments of the procedure can also be performed using a guide sleeve 360. As shown in FIG. 10A, the guide sleeve 360 can comprise a hollow body 362 that is configured to correspond to the cross-sectional shape of the osteotomy prepared by the trephine drill or other tool. Thus, in some embodiments, the body 362 is generally a hollow tubular or cylindrical shape that generally corresponds to the shape of the trephine drill in order to ensure that the sleeve 360 can be placed at or within the osteotomy created by the drill. In such embodiments, the hollow body 362 has an inner and outer diameter that substantially corresponds to the inner and outer diameter of the trephine drill.

The cross-sectional view of FIG. 10B illustrates the placement of the guide sleeve 360 in an osteotomy 370 created at the target site 372. In this manner, the guide sleeve 360 can be used for subsequent steps in the procedure, as described herein, that further modify the target site in order to create a prepared site that is capable of receiving a dental implant. In particular, the guide sleeve 360 can serve to ensure that additional tools used in the procedure are properly aligned relative to the osteotomy 370. For example, in some embodiments, the sleeve 360 can be used to coaxially or vertically align additional tools relative to the osteotomy 370. Further, other embodiments described herein allow additional tools to be horizontally aligned or controlled using the sleeve 360, such as limiting the depth of such tools.

In some embodiments, the guide sleeve 360 can comprise a transverse flange 374 at a proximal end 376 thereof. The flange 374 can be used to facilitate handling of the sleeve 360 during placement and removal of the sleeve 360. In addition, some embodiments of the procedure can provide that the sleeve 360 is used with a guide tool, such as the guide tool 260 described above. Such an embodiment of the procedure is shown in FIG. 10C. Thus, a guide tool 380 can be used by a surgeon to place the sleeve 362 at an osteotomy of a target site 382.

Referring now to FIGS. 11A-C, and additional aspect of embodiments of the procedure is shown. FIG. 11A illustrates an embodiment of an interradicular burr or bone coring tool 400 that can be used in preparation of the target site. The term "coring" can refer generally to the process of drilling into the bone of the patient in order to remove bone material and to prepare the osteotomy. Although the tool 400 is referred to as a coring tool, it is contemplated that the coring process can be performed using a variety of other tools and guides, as described herein. The coring process can also refer to the process of removing a portion of the bone post such that the bone post defines a selected height.

The bone coring tool 400 may be necessary in order to achieve the prepared site 110 shown in FIG. 4. The tool 400 can optionally be used in embodiments of the procedure. The tool 400 can comprise an elongate body, a distal cutting face 402, and a plurality of flutes 404 that run lengthwise along the elongate body of the tool 400.

In addition, the tool 400 can comprise one or more torque transmitting sections 406 disposed along a shaft 408 of the tool 400 which can be engaged, along with a proximal engagement section 410, by a turning instrument in order to rotate the tool 400. The torque transmitting section 406 can be formed as a hex or other geometric shape configured to provide secure engagement and transfer of torque between a turning instrument and the tool 400. Further, the use of the torque transmitting section 406 can ensure that the shaft 408 of the tool 400 does not jam in the turning instrument, which may commonly occur if only the proximal engagement section 410 is used due to the significant torque that is exerted on the proximal engagement section 410.

In some embodiments, the tool 400 can be placed into a guide sleeve 420 that has been placed in an osteotomy 422 at a target site 424 in order to perform a coring procedure. The guide sleeve 420 can be configured in a manner similar to that of the guide sleeve 360 described above. The tool 400 can therefore be configured to fit within the interior diameter of the sleeve 420. In this manner, a longitudinal axis of the tool 400 can be substantially coaxially aligned with a longitudinal axis of the osteotomy 422. For example, the outer diameter of the tool 400 can be configured relative to the inner diameter of the sleeve 420 such that only a small gap is present between the sleeve 420 and the tool 400. In some embodiments, the gap is approximately between 0.05 mm to 0.3 mm.

In addition, the tool 400 can comprise a limit flange or portion 434 that can contact an upper portion 436 of the guide sleeve 420. The upper portion 436 of the guide sleeve 420 can be formed as a circular edge, a flange, a movable component, or one or more protrusions extending from the guide sleeve 420. In this regard, the length of the tool 400 and the length of the guide sleeve 420 can be configured such that the tool 400 is permitted to descend into the guide sleeve 420 and cut into the bone post 430 up until contact occurs between the limit flange 434 of the tool 400 and the upper portion 436 of the guide sleeve 420. The contact between the limit flanges 434 and the upper portion 436 can limit the depth to which the tool 400 can penetrate, as shown in FIG. 11C. As such, the bone post 430 can be formed to a specific height 438 and diameter. In some embodiments, the tool 400 of the sleeve 420 can be configured such that the resultant bone post 430 has a height of approximately 2 mm. However, the height of the bone post 430 can be selectively adjusted by altering one of the length of the tool 400 or the length of the sleeve 420. Accordingly, by using the sleeve 420, the bone post 430 can be cut to a desired dimension while ensuring that the tool 400 does not contact or damage the sides of the osteotomy.

For example, it is contemplated that the tool 400 can be configured such that the height 438 of the bone post 430 is determined by the difference between a effective longitudinal length 442 of the tool 400 and an effective longitudinal length 444 of the guide sleeve 420. The length 442 of the tool 400 can be calculated as the distance from the flange 434 thereof to the distal end of the tool 400. Accordingly, when the tool 400 is inserted into the guide sleeve 420, the flange 434 can eventually contact the upper portion 436 of the sleeve 420 to prevent further axial movement of the tool 400 into the sleeve 420. As shown in FIG. 11C, embodiments provide that the effective longitudinal length 444 of the sleeve 420 is greater than the operative longitudinal length 442 of the tool 400, thus allowing the bone post 430 to remain within and have its height 438 extending into the sleeve 420.

It is also contemplated that a plurality of tools 400 can be provided that each defines different operative longitudinal lengths 442. Depending on a given procedure, a surgeon could select a given tool 400 based on the needed dimensions of the bone post. Further, a plurality of guide sleeves 420 could be provided that each defines different longitudinal lengths 444 in order to allow the surgeon to configure the bone post as desired.

Additionally, the tool 400 and/or the sleeve 420 can be configured such that the respective lengths 442, 444 thereof are selectively adjustable. For example, the flange 434 can be translatable along the longitudinal axis of the tool 400 in order to adjust the operative longitudinal length 442 of the tool 400. The flange 434 could be adjustable to one of a plurality of positions along the tool 400. The flange 434 can be adjusted using snap fit, rotational locking, or other means for adjusting and fixing the axial position of the flange 434. Indeed, the positions could allow adjustment of the operative longitudinal length 442 in 0.5 mm or 1 mm increments. Similarly, the length 444 of the sleeve 420 can be selectively adjusted using similar means.

Accordingly, when rotated, the cutting face 402 of the tool 400 will cut into a bone post 430 formed by the osteotomy 422 to thereby create a planar top surface 432 on the bone post 430. Accordingly, the bone post 430 can take on a shape that is generally cylindrical and have a top surface 432 that is oriented generally perpendicular relative to a longitudinal axis of the bone post 430. As will be described further herein, the formation of a finished bone post 430 can allow a tubular dental implant such as those described herein to be received at the target site. In particular, and in some embodiments, the geometry of the bone post 430 can be configured to correspond to the geometry of a dental implant and can contribute to the stability and fit of the implant at the target site.

During the coring procedure, bone material 440 that is removed from an upper section of the bone post 430 can be received within the flutes 404 of the tool 400, as shown in FIG. 11D. The bone material 440 can be advantageously collected using the sleeve 420 described above. The sleeve 420 can provide a non-compressible, non-porous surface against which the bone material can be pressed and urged into the flutes 404 of the tool 400. Further, residual bone material can also be collected from within the sleeve 420 when the coring process is finished.

The collection of bone material during the coring process can provide a surgeon with bone material that can later be grafted into portions or sockets of the target site. It is generally know that autogenous bone material is more likely to be successfully grafted into a given bone area. However, in accordance with at least one of the embodiments disclosed herein is the realization that bone material can be collected during the implant placement procedure and can later be used to fill in gaps at the target site. As such, although in implant will be generally stable when installed in the annular space of a prepared site, the bone material collected during the procedure can be grafted into the sockets around the implant such that the implant will be even more securely retained once the graft is healed.

In accordance with another embodiment, the dental implant placement procedure can optionally comprise the step of tapping the osteotomy to create a series of threads along an outer surface of the bone post and/or the inner surface of the cavity formed by the osteotomy. If needed, a tapping tool can be used to further configure the prepared site 110 referred to in FIG. 4. This optional step can be performed when placing an implant into dense bone.

Figure 12A:
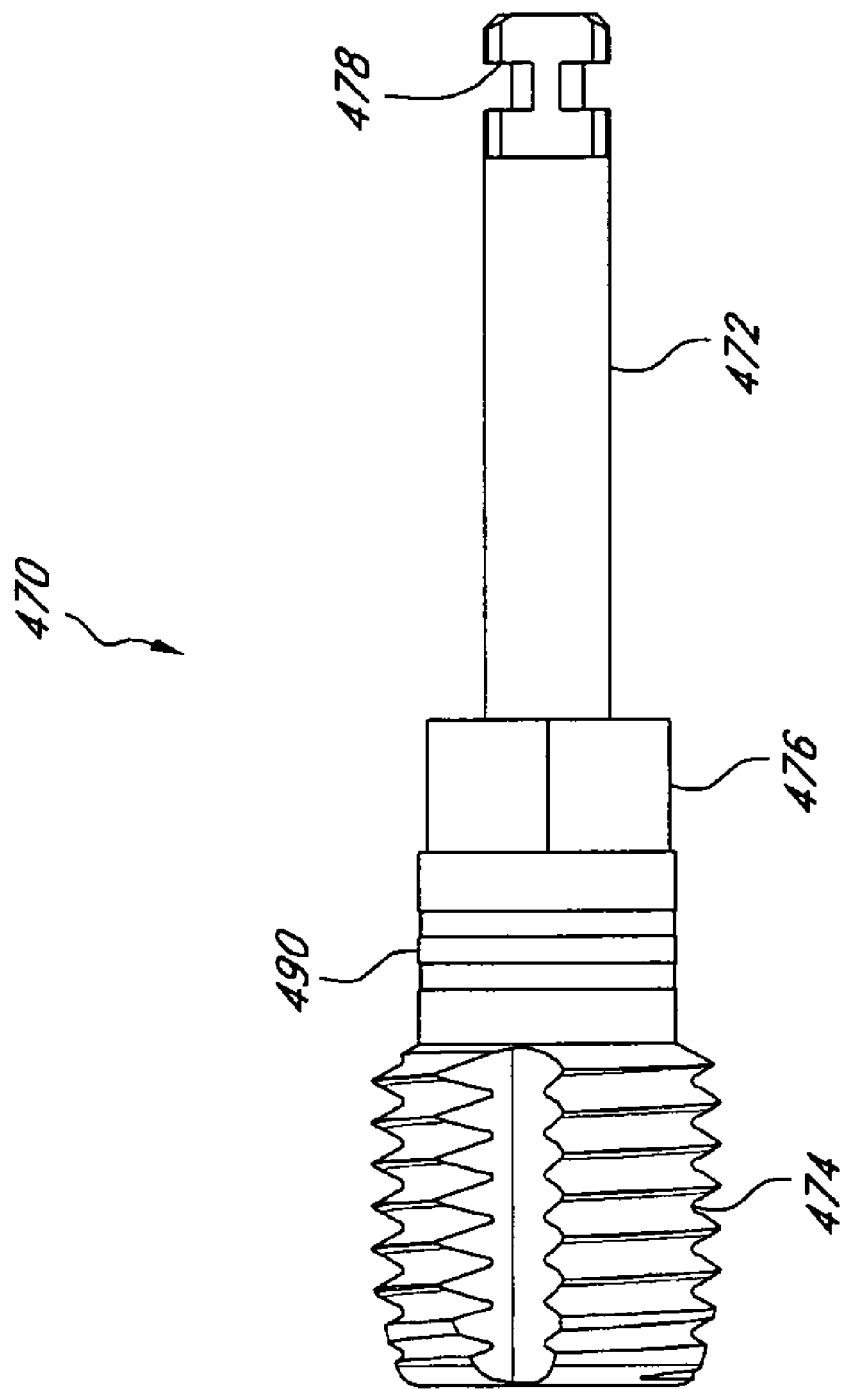
FIG. 12A is a perspective view of a tap tool in accordance with an embodiment.
Figure 12B:
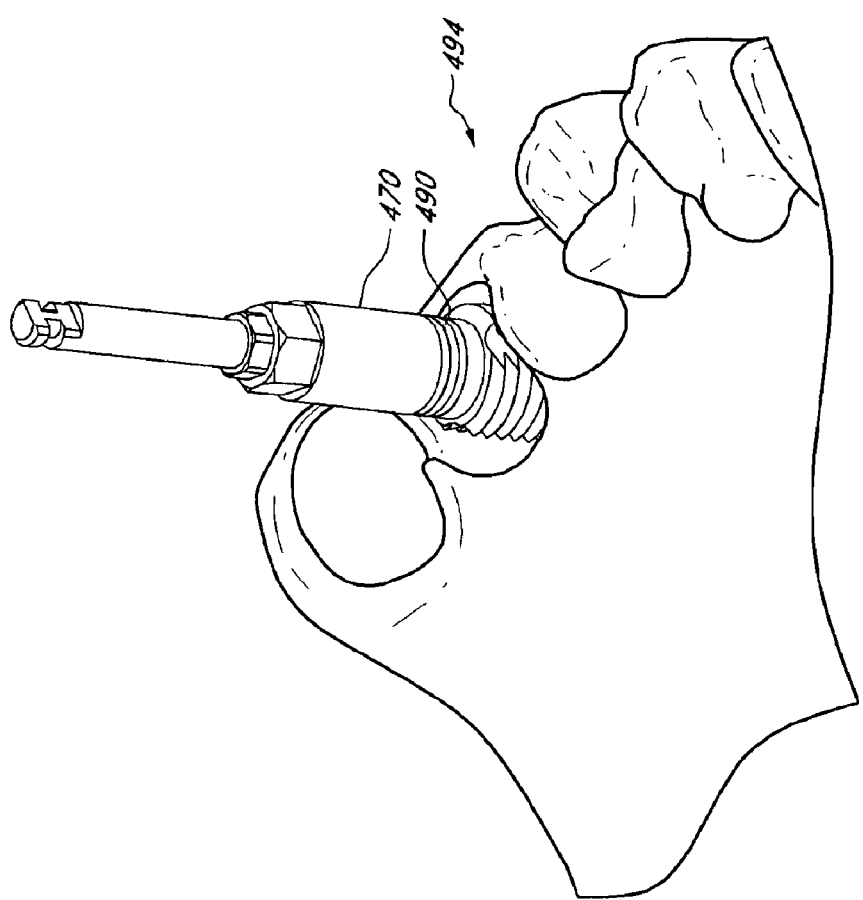
FIG. 12B is a perspective view of a target site at which the tap tool is used, according to an embodiment.

FIGS. 12A-B illustrate a tapping tool 470 and an exemplary manner of use. The tapping tool 470 can comprise an elongate shaft 472 that is coupled to a tapping portion 474 located at a distal end of the shaft 472. In addition, the shaft can comprise one or more torque transmitting sections 476 which can be engaged, along with a proximal engagement section 478, by a turning instrument in order to rotate the tool 470. The torque transmission section 476 can be formed as a hex or other geometric shape configured to provide secure engagement and transfer of torque between a turning instrument and the tool 470. Further, the use of the torque transmitting section 476 can ensure that the shaft 472 of the tool 470 does not jam in the turning instrument, which may commonly occur if only the proximal engagement section 478 is used due to the significant torque that is exerted on the proximal engagement section 478.

Additionally, some embodiments of the tapping tool 470 can comprise one or more depth markers 490. As such, during the tapping process, the tool 470 can be inserted up to a desired depth at an target site 494 which can be monitored using the depth markers 490. Further, the tool 470 can be configured to define a length of approximately 5 mm. However, it is contemplated that the length of the tool 470 can be increased or decreased in order to allow a surgeon greater flexibility and versatility during the implantation process. Furthermore, the diameter of the tapping portion 474 can also be varied in order to correspond to the diameter of a given osteotomy. For example, it is contemplated that a plurality of tapping tools 470 can be available to the surgeon in order to accommodate length and diameter requirements of the tool 470 for a given procedure.

FIG. 13 is a perspective view of a try-in component 500. The try-in component 500 can be used as a temporary prosthetic that simulates how a new implant and/or abutment would be received and fit into the prepared site. The component 500 can therefore simulate either a one-piece implant or a multi-piece implant. The try-in component 500 can comprise a body portion 502 and an upper portion 504. In the embodiment illustrated in FIG. 13, the try-in component 500 includes a hollow interior 506 within the body 502. In addition, the try-in component 500 can comprise a circumferential groove 508 that extends about the body portion 502. The groove 508 can be configured to indicate, for example, a transition point from an implant portion to an abutment portion for a single-piece implant, or for a multi-piece implant, a transition point from the implant to an abutment.

The try-in component 500 can be configured to mimic the dimensions of a dental implant. For example, the try-in component 500 can be configured such that it defines an overall height that matches an overall height of a dental implant and/or an abutment that can be attached to the dental implant. The location of the circumferential groove 508 can correspond to a height of the threads of an implant or to a top surface of an implant. Additional important dimensions, such as the shape of the upper portion 504, the depth of the hollow interior 506, and the diameter taken along one or more points on the body portion 502 can likewise be configured to match those of a corresponding dental implant.

In use, in embodiments of the procedure, the try-in component 500 can be placed at a prepared site, such as the prepared site 110 illustrated in FIG. 4. Because the try-in component 500 has been configured to generally match or approximate the important dimensions of a corresponding dental implant, the component 500 can be placed and observed in order to determine whether the corresponding implant would properly fit at the prepared site. For example, one of the observations that can be made is whether the annular space extends to a sufficient depth for receiving the implant. As noted above, the component 500 can include a groove 508 that corresponds to the thread height or top surface of the implant and that can serve as a visual indicator as to whether the annular space extends to a sufficient depth. Additionally, the upper portion 504 of the component 500, which can correspond to an upper portion of an implant and/or an abutment that has been attached to the implant, can be compared relative to the surrounding dentition and can be checked for clearance under occlusion.

Figure 14C:
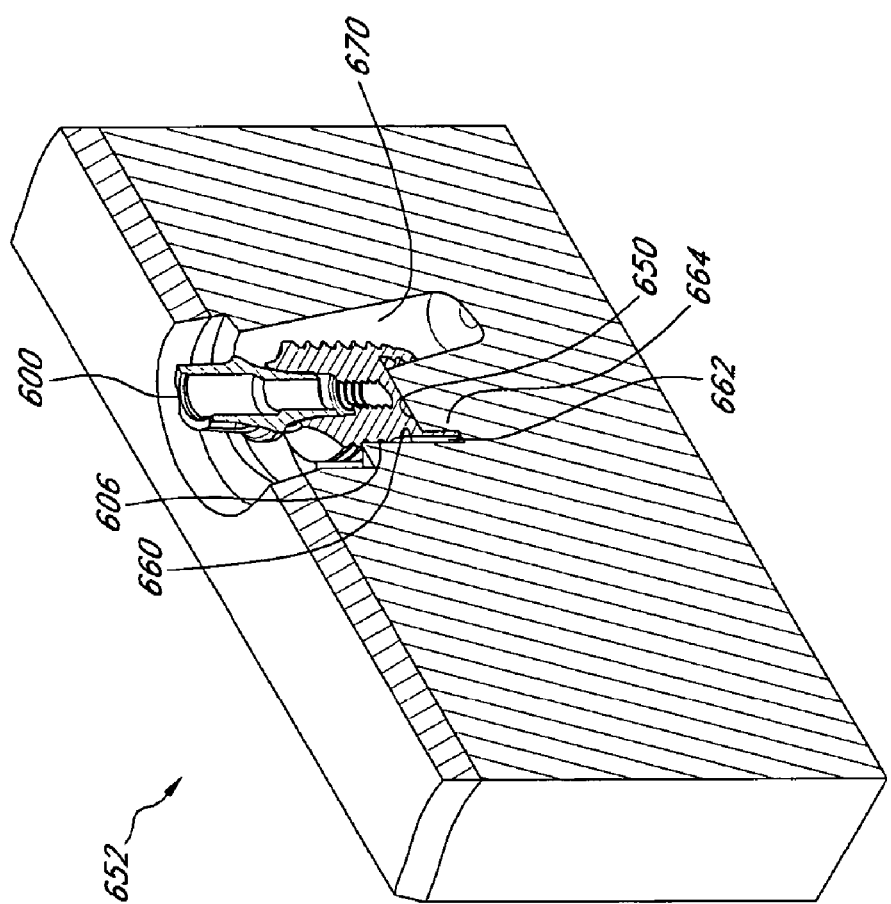
FIG. 14C as a cross-sectional perspective view of the implant of FIG. 14A being placed at a prepared extraction site, according to an embodiment.

FIGS. 14A-C illustrates an embodiment of a dental implant 600 that can be used in accordance with an embodiment of the dental implant placement procedure discussed herein. As shown, the implant 600 can be configured as a single-piece implant. The implant 600 can comprise a threaded portion 602 and an abutment portion 604. The implant 600 can comprise engaging means for engaging at least a portion of the prepared site. In some embodiments, the engaging means can comprise a plurality of threads 606 that are disposed along the threaded portion 602. However, other structures can also be utilized to secure the implant 600 relative to the bone.

Additionally, as shown in FIG. 14B, the implant 600 can comprise an inner cavity 620 that extends at least partially from a bottom face 622 of the implant 600 toward a top face 624 thereof. The inner cavity 620 and the bone post of the prepared site can be configured to correspond to each other such that when the implant 600 is seated or installed in the prepared site, the bone post is generally engaged by the inner cavity 620. In this regard, the inner cavity 620 can be approximately 1.9 mm in depth in order to correspond to a bone post having a height of approximately 2 mm. However, other configurations can be prepared wherein the heights of the inner cavity and the bone post correspond to each other. Further, the engaging means of the implant 600 can further comprise a plurality of threads 626 that are disposed along and interior surface of the inner cavity 620. In some embodiments, such as that illustrated in FIG. 14B, the threads 626 can be configured as internal threads.

The implant 600 can also comprise a tool engagement portion 640 extending from the top face 624 towards the bottom face 622 of the implant 600. The engagement portion 640 can comprise a socket 644 that is configured to mate with a turning tool such that a torque from the turning tool can be effectively transferred to the implant 600. As illustrated, the socket 644 can be configured as a hexagon. However, it is contemplated that the socket 644 can be any variety of geometric shapes, such as triangular, square, or any other screw drive types, such as philips, pozidriv, torx, tri-wing, torq-set, or triple-square, to name a few. In addition, the tool engagement portion 640 can also comprise a conical and threaded connection 642 that can be used to couple an abutment to the implant.

FIG. 14C illustrates installation of the implant 600 into a prepared site 650 created at a target site 652. As shown, the threads 606 of the installed implant 600 can engage a cavity or wall 660 of an annular space 662 of the prepared site 650. Further, the threads 626 can also engage a bone post 664 of the prepared site 650. Finally, it is also noted that in some embodiments of the procedure, bone material may have been collected during the coring procedure using the inter-radicular burr or coring tool. Thus, with respect to FIG. 14C, it is noted that a tooth socket 670 can be filled with the bone material collected during the coring procedure. As a result, in addition to the engagement between the threads 606 and the wall 660 and the engagement between the threads 626 and the bone post 664, which sufficiently anchors the implant 600 at the target site 652, the grafting of bone material into the tooth sockets can enhance the engagement between the implant 600 and the target site 652.

Figure 15:
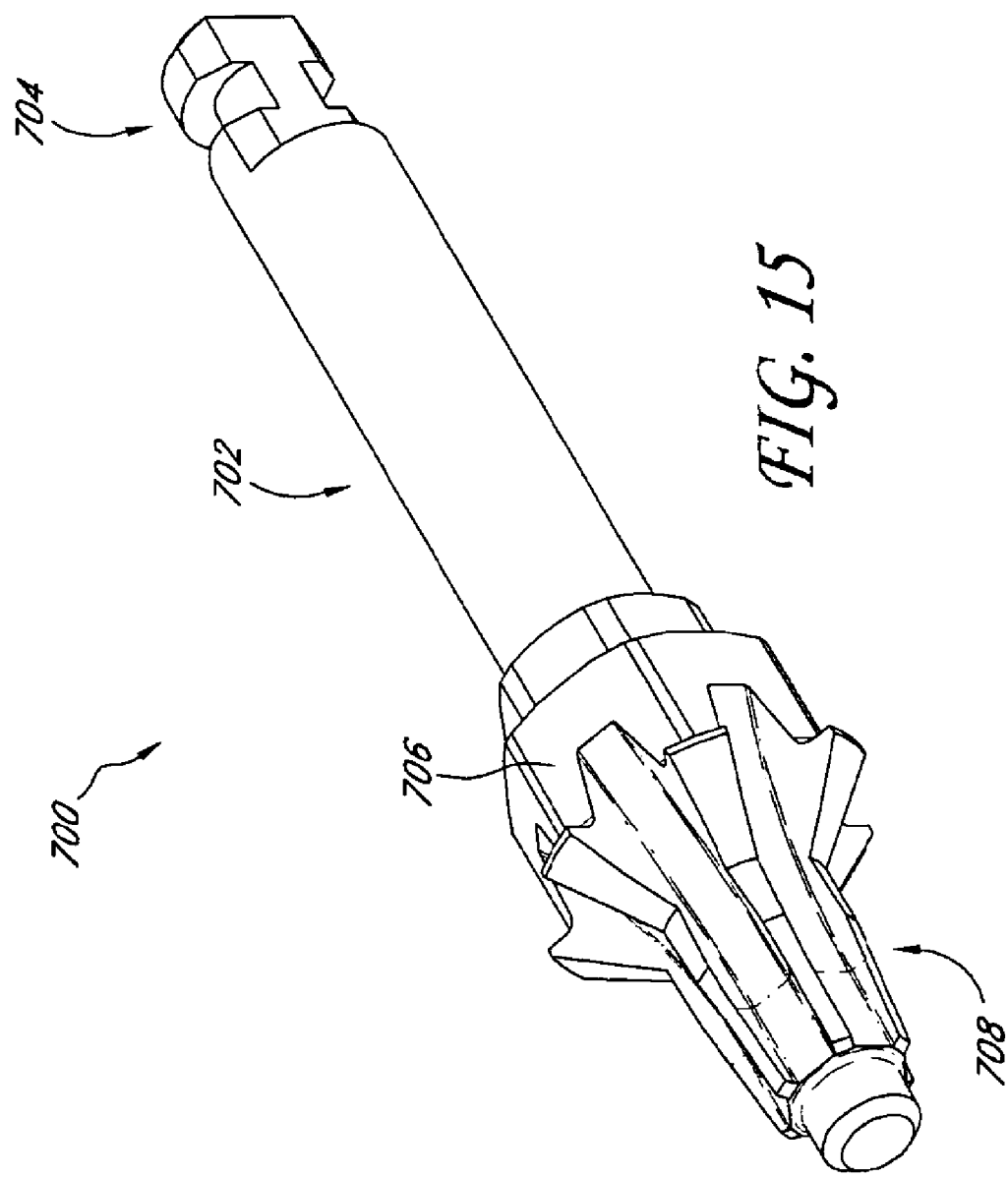
FIG. 15 is a perspective view of an implant driver in accordance with an embodiment.

With reference now to FIG. 15, and implant driver 700 is shown. The implant driver can comprise an elongate shaft 702, a proximal engagement section 704, a torque transmitting section 706, and an implant driving section 708. The driver 700 can be attached to a turning instrument by means of the proximal engagement section 704, which can allow a torque from the turning instrument to be transmitted to the driver 700. The implant driving section 708 can be configured to mate with a tool engagement portion of an implant for driving or turning the implant in order to install the implant.

In some embodiments, the driver 700 can comprise one or more torque transmitting sections 706 disposed along the shaft 702 which can be engaged, along with a proximal engagement section 704, by the turning instrument in order to rotate the driver 700. The torque transmitting section 706 can be formed as a hex or other geometric shape configured to provide secure engagement and transfer of torque between a turning instrument and the driver 700. Further, the use of the torque transmitting section 706 can ensure that the shaft 702 of the driver 700 does not jam in the turning instrument, which may commonly occur if only the proximal engagement section 704 is used due to the significant torque that is exerted on the proximal engagement section 704. Finally, the implant driving section 708 can be formed as a tip that includes one or more radially extending protrusions. In some embodiments, the implant driving section 708 can comprise 4, 6, or 8 radially extending protrusions. These protrusions can be arranged in a pattern in which the protrusions lie circumferentially equidistant relative to each other. However, the protrusions can also be arranged in a variable circumferential spacing about the implant driving section 708.

In accordance with another embodiment, FIGS. 16-20 illustrate an implant driver 800 that can be used to install an embodiment of the implants discussed herein. The driver 800 can comprise an elongate shaft 802, a proximal engagement section 804, a torque transmitting section 806, and an implant driving section 808. Similarly to the implant driver 700 discussed above, the driver 800 can be attached to a turning instrument by means of the proximal engagement section 804, which can allow a torque from the turning instrument to be transmitted to the driver 800. The implant driving section 808 can be configured to mate with a tool engagement portion of an implant for driving or turning the implant in order to install the implant.

In addition, some embodiments of the driver 800 can be configured to include one or more torque transmitting sections 806. The one or more torque transmitting sections 806 can be disposed along the shaft 802. The one or more torque transmitting sections 806 can be engaged, along with the proximal engagement section 804, by a turning instrument in order to rotate the driver 800. The torque transmitting section 806 can be formed as a hex or other geometric shape configured to provide secure engagement and transfer of torque between a turning instrument and the driver 800.

The implant driver 800 can optionally include one or more retention structures 810. The retention structure 810 may be used to facilitate interaction between the implant driver and the implant or between the implant driver and the turning instrument. For example, the retention structure 810 may aid in removably coupling the implant driver to the implant or the implant driver to the turning instrument.

Figure 16:
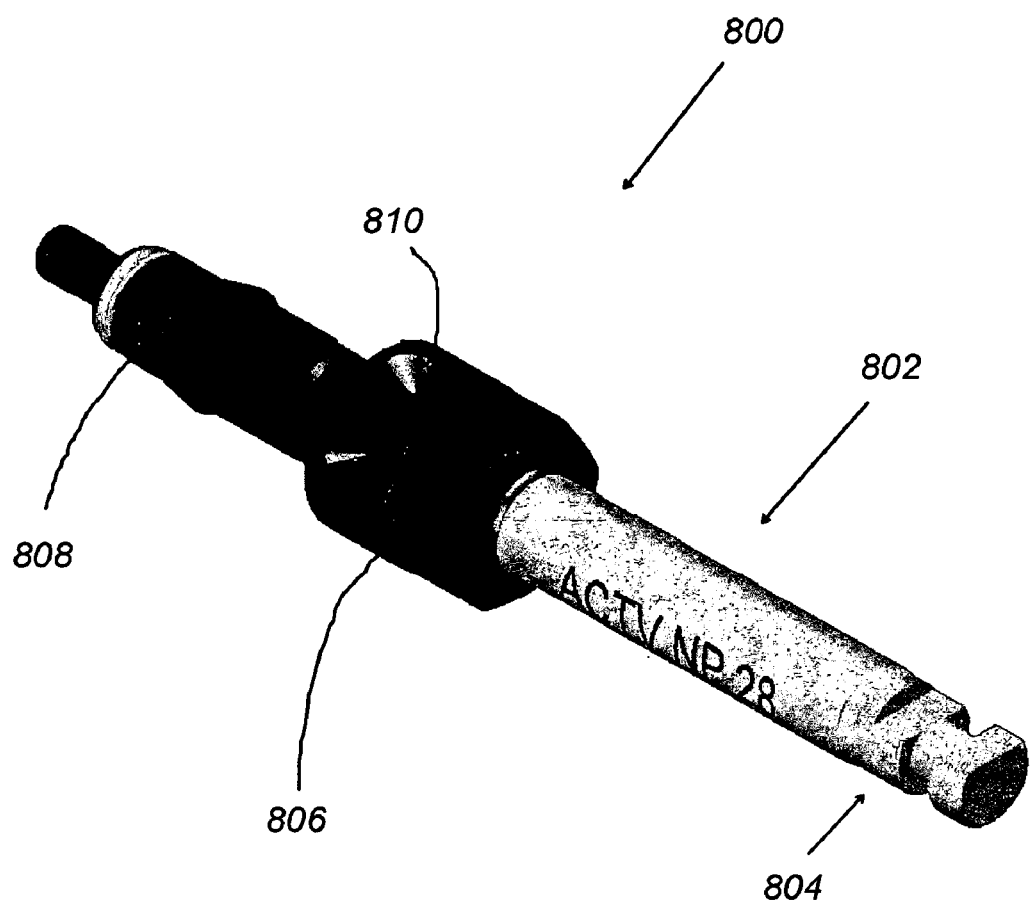
FIG. 16 is a perspective view of another implant driver in accordance with an embodiment.
Figure 17:
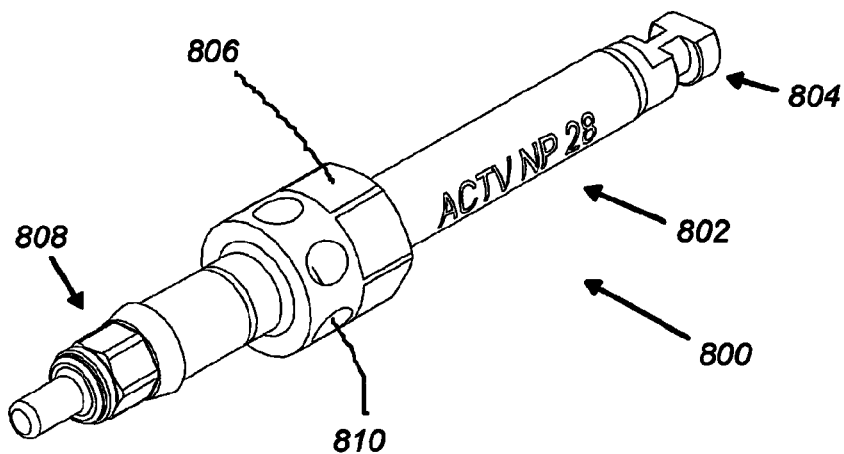
FIG. 17 is another perspective view of the implant driver of FIG. 16.
Figure 18:
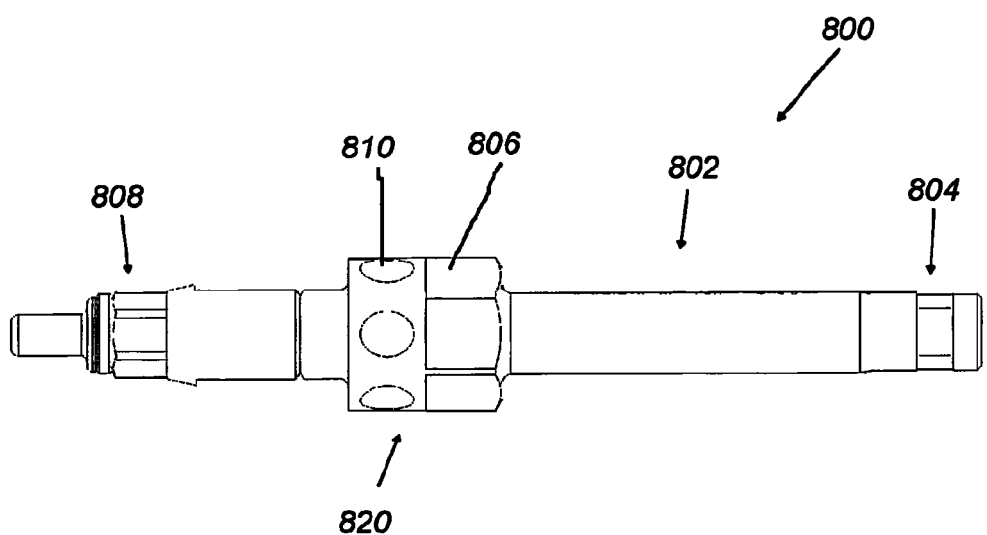
FIG. 18 is a side view of the implant driver of FIG. 16.

The retention structure is 810 can be disposed along the elongate shaft 802 of the driver 800. As illustrated in FIGS. 16-18, the retention structure 810 can be disposed adjacent to the torque transmitting section 806. In the illustrated embodiment, the retention structures 810 can be disposed intermediate the torque transmitting section 806 and the implant driving section 808.

The embodiment illustrated in FIG. 16 shows that the retention structure 810 can comprise a plurality of indentations. These indentations can be circumferentially spaced about a portion of the implant driver 800. In some embodiments, the indentations can be generally conical in shape; however, various other shapes can be used. As shown in FIGS. 16-18, the retention structure 810 can be monolithically formed with the torque transmitting section 806. Such an embodiment may advantageously allow quick and secure engagement between the implant driver 800 and the turning instrument. It is also contemplated that the retention structure 810 can also comprise a plurality of protrusions or bumps. Such protrusions can be circumferentially spaced about a portion of the implant driver 800.

Additionally, the embodiment illustrated in FIGS. 16-18 can also comprise an alignment portion 312. The alignment portion 312 can extend from a distal end of the driver 800. The alignment portion 312 can be received to within a connection aperture of an implant, such as a threaded hole thereof. In this regard, the alignment portion 312 can be a generally cylindrical, conical, or other shape that allows the alignment portion 312 to aid in centering the driver 800 as the distal end of the driver 800 is inserted into the implant.

Figure 19:
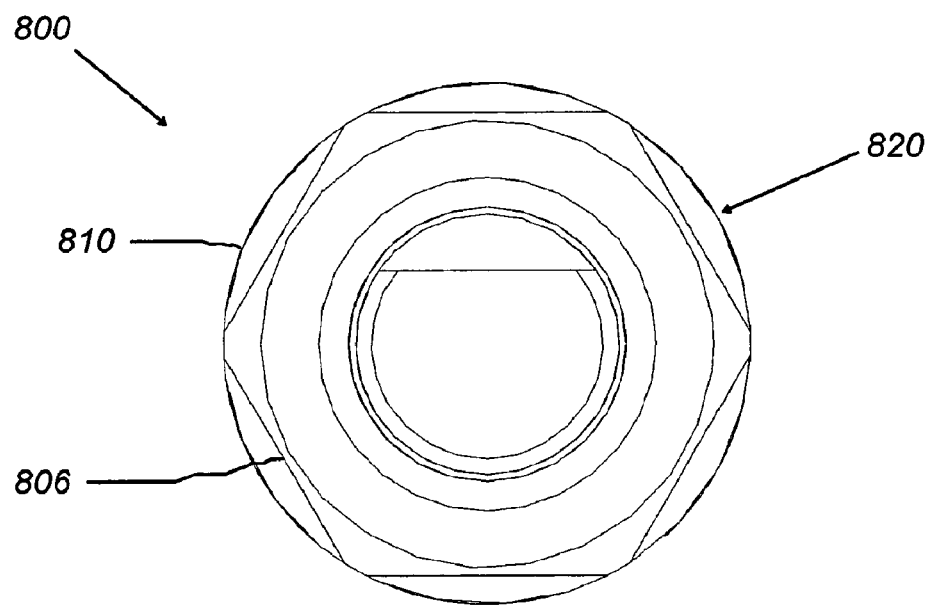
FIG. 19 is an end view of a proximal end of the implant driver of FIG. 16.
Figure 20:
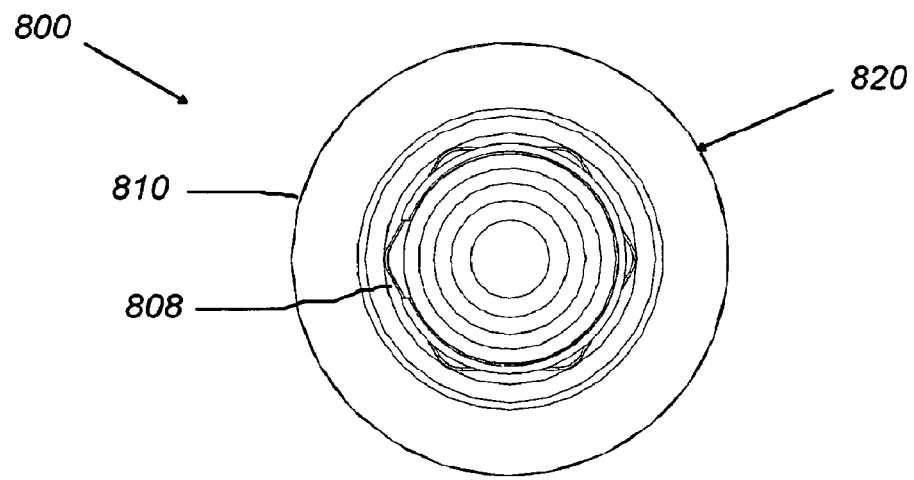
FIG. 20 is an end view of a distal end of the implant driver of FIG. 16.

FIGS. 19 and 20 are end views of the implant driver 800. FIG. 19 is a proximal end view illustrating a hexagonal configuration of the torque transmitting section 806 in accordance with an embodiment. This embodiment, as illustrated in FIGS. 16-19, can be configured such that a portion 820 of the driver 800 forms the torque transmitting section 806 and the retention structure 810. In an embodiment, the portion 820 of the driver 800 can comprise a generally cylindrical structure in which the retention structure 810 is formed and a multifaceted structure in which the torque transmitting section 806 is formed. As illustrated in FIG. 19, the cylindrical structure of the portion 820 can have a greater cross-sectional geometry than the multifaceted structure. Such a feature may be advantageous in facilitating engagement between the implant driver 800 and a turning instrument.

FIG. 20 is an end view of a distal end of the implant driver 800. As illustrated, the implant driving section 808 can be hexagonally shaped. In some embodiments, the implant driving section 808 can have a smaller cross-sectional profile than the portion 820 of the driver 800. Further, it is contemplated that the implant driving section 808 can be configured as a geometric shape other than a hexagon. For example, the implant driving section 808 can be configured in a variety geometrics shapes such is triangular, square, and various other shapes that may correspond with a slotted screw drive, such as those listed above.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. A combination for creating a prepared site for a dental implant, the combination comprising:
    a trephine drill defining inner and outer diameters;
    an interradicular burr defining an outer diameter being less than the outer diameter of the trephine drill; and
    a guide sleeve defining inner and outer diameters, the outer diameter being approximately equal to the outer diameter of the trephine drill, the inner diameter being approximately equal to the inner diameter of the trephine drill, the guide sleeve being configured to removably receive the interradicular burr therein, wherein the guide sleeve comprises an upper portion at a proximal end thereof, wherein the interradicular burr includes a corresponding limit flange configured to contact the upper portion of the guide sleeve when the interradicular burr is inserted into the guide sleeve, and wherein when the interradicular burr is inserted into the guide sleeve and the corresponding limit flange contacts the upper portion of the guide sleeve, the interradicular burr defines an operational longitudinal length such that a distal end of the interradicular burr does not extend beyond the guide sleeve.

2. The combination of claim 1, wherein the interradicular burr defines the operational longitudinal length less than an effective longitudinal length of the guide sleeve.

* * * * *